US012590294B2

(12) United States Patent

Lei et al.

(10) Patent No.: US 12,590,294 B2

(45) Date of Patent: Mar. 31, 2026

(54) PROCESS FOR PRODUCING CARDIOMYOCYTES

(71) Applicant: Oxford University Innovation Limited, Oxford (GB)

(72) Inventors: Ming Lei, Oxford (GB); Derek Terrar, Oxford (GB); Faizzan Ahmad, New York, NY (US)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 704 days.

(21) Appl. No.: 17/786,122

(22) PCT Filed: Jan. 21, 2021

(86) PCT No.: PCT/EP2021/051297

§ 371 (c)(1), (2) Date: Jun. 16, 2022

(87) PCT Pub. No.: WO2021/148516

PCT Pub. Date: Jul. 29, 2021

(65) Prior Publication Data

US 2023/0045742 A1 Feb. 9, 2023

(30) Foreign Application Priority Data

Jan. 22, 2020 (GB) ..................................... 2000903

(51) Int. Cl.

*C12N 5/077* (2010.01)

(52) U.S. Cl.

CPC ...... *C12N 5/0657* (2013.01); *C12N 2501/155* (2013.01); *C12N 2501/385* (2013.01); *C12N 2501/415* (2013.01); *C12N 2506/45* (2013.01)

(58) Field of Classification Search

None

See application file for complete search history.

(56) References Cited

FOREIGN PATENT DOCUMENTS

| | | | | |
|---|---|---|---|---|
| CN | 108359636 A | 8/2018 | | |
| WO | 2004/011603 A2 | 2/2004 | | |
| WO | 2008/040027 A2 | 4/2008 | | |
| WO | 2008/112323 A1 | 9/2008 | | |
| WO | 2009/114673 A2 | 9/2009 | | |
| WO | 2010/007031 A2 | 1/2010 | | |
| WO | 2011/157029 A1 | 12/2011 | | |
| WO | WO-2017164746 A1 * | 9/2017 | .......... | C12N 5/0657 |
| WO | 2018/098597 A1 | 6/2018 | | |

OTHER PUBLICATIONS

Yuan, Meng. Atrial cardiomyocytes development from human induced pluripotent stem cells. Diss. University of Oxford, 2018. (Year: 2018).*

Rodriguez P, & Kranias EG Phospholamban: a key determinant of cardiac function and dysfunction. Arch Mal Coeur Vaiss 98: 1239-1243. (2005).

Yamamoto-Hino M, Sugiyama T, Hikichi K, Mattei MG, Hasegawa K, Sekine S, et al. Cloning and characterization of human type 2 and type 3 inositol 1,4,5-trisphosphate receptors. Receptors Channels 2: 9-22. (1994).

Brodde et al., 1999 Adrenergic and muscarinic receptors in the human heart. Pharmacological Reviews vol. 51, No. 4.

International Search Report and Written Opinion for WO 2021/148516 (PCT/EP2021/051297), dated Apr. 26, 2021, pp. 1-19.

UK Search Report for GB 2000903.1, dated Jul. 15, 2022, pp. 1-4.

Tanwar Vineeta et al: "Gremlin 2 Promotes Differentiation of Embryonic Stem Cells to Atrial Fate by Activation of he JNK Signaling Pathway: Grem2 Enhances Atrial Differentiation of ESCs", Stem Cells, vol. 32, No. 7, Jun. 17, 2014 (Jun. 17, 2014), pp. 1774-1788.

Bylund Jeffery B. et al: "Differentiation of Atrial Cardiomyocytes from Pluripotent Stem Cells Using the BMP Antagonist Grem2", Journal of Visualized Experiments, No. 109, Mar. 10, 2016 (Mar. 10, 2016).

Bylund Jeffery B. et al: "Coordinated Proliferation and Differentiation of Human-Induced Pluripotent Stem Cell-Derived Cardiac Progenitor Cells Depend on Bone Morphogenetic Protein Signaling Regulation by GREMLIN 2", Stem Cells and Development, vol. 26, No. 9, May 1, 2017 (May 1, 2017), pp. 678-693.

Grandi Eleonora et al: "Human Atrial Action Potential and Ca 2+ Model: Sinus Rhythm and Chronic Atrial Fibrillation", Circulation Research, vol. 109, No. 9, Oct. 14, 2011 (Oct. 14, 2011), pp. 1055-1066.

Chunhui Xu: "Differentiation and enrichment of cardiomyocytes from human pluripotent stem cells", Journal of Molecular and Cellular Cardiology, Academic Press, GB, vol. 52, No. 6, Mar. 20, 2012 (Mar. 20, 2012), pp. 1203-1212.

H. D. Devalla et al: "Atrial-1ike cardiomyocytes from human pluripotent stem cells are a robust preclinical model for assessing atrial-selective pharmacology", EMBO Molecular Medicine, vol. 7, No. 4, Feb. 19, 2015 (Feb. 19, 2015), pp. 394-410.

Lukas Cyganek et al: "Deep phenotyping of human induced pluripotent stem cell-derived atrial and ventricular cardiomyocytes", JCI Insight, vol. 3, No. 12, Jun. 21, 2018 (Jun. 21, 2018).

International Preliminary Report on Patentability for WO 2021/148516 (PCT/EP2021/051297), dated Jul. 26, 2022, pp. 1-9.

(Continued)

*Primary Examiner* — Tracy Vivlemore

*Assistant Examiner* — Fatimah Khalaf Matalkah

(74) *Attorney, Agent, or Firm* — Thomas|Horstemeyer, LLP

(57) ABSTRACT

The present invention relates to a process for producing a population of cells which comprises mature atrial cardiomyocytes. The process comprises the step of treating iPS cells according to a treatment regimen which comprises contacting the iPS cells with Gremlin2 and retinoic acid, such that at least a portion of the iPS cells differentiate into mature atrial cardiomyocytes.

11 Claims, 25 Drawing Sheets

Specification includes a Sequence Listing.

(56) References Cited

OTHER PUBLICATIONS

Takahashi K, Yamanaka S "Induction of pluripotent stem cells from mouse embryonic and adult fibroblast cultures by defined factors". Cell. 126 (4): 663-76 (Aug. 2006).
Guo XL, Chen JS "Research on induced pluripotent stem cells and the application in ocular tissues". International Journal of Ophthalmology. 8 (4): 818-25 (2015).
Shi Y, Inoue H, Wu JC, Yamanaka S "Induced pluripotent stem cell technology: a decade of progress". Nat Rev Drug Discov. Feb. 2017;16(2):115-130. doi: 10.1038/nrd.2016.245. Epub Dec. 16, 2016.
Sayed N, Liu C, Wu JC "Translation of Human-Induced Pluripotent Stem Cells: From Clinical Trial in a Dish to Precision Medicine". J Am Coll Cardiol. May 10, 2016;67(18):2161-2176. doi: 10.1016/j.jacc.2016.01.083.
Matsa E, Burridge PW, Wu JC "Human stem cells for modeling heart disease and for drug discovery", Sci Transl Med. Jun. 4, 2014;6(239):239ps6. doi: 10.1126/scitranslmed.3008921.
Hockemeyer D, Jaenisch R "Induced Pluripotent Stem Cells Meet Genome Editing". Cell Stem Cell. 18 (5): 573-86 (2016).
Yu J, Vodyanik MA, Smuga-Otto K, Antosiewicz-Bourget J, Frane JL, Tian S, Nie J, Jonsdottir GA, Ruotti V, Stewart R, Slukvin II, Thomson JA "Induced pluripotent stem cell lines derived from human somatic cells". Science. 318 (5858):1917-20 (2007).
Burridge et al. "Chemically defined generation of human cardiomyocytes". Nat Methods. 2014;11:855-860.
Burridge et al. "Chemically Defined Culture and Cardiomyocyte Differentiation of Human Pluripotent Stem Cells" Curr. Protoc. Hum. Genet. 2015; 87: 21.3.1-21.3.15.
Gonzalez R, et al. "Stepwise chemically induced cardiomyocyte specification of human embryonic stem cells". Angew Chem Int Ed Engl. 2011;50:11181-11185.
Lian X, et al. "Robust cardiomyocyte differentiation from human pluripotent stem cells via temporal modulation of canonical Wnt signaling". Proc. Natl. Acad. Sci. U S A. 2012;109:E1848-1857.
Willems E, et al. "Small-molecule inhibitors of the Wnt pathway potently promote cardiomyocytes from human embryonic stem cell-derived mesoderm". Circulation Research. 109 (4): 360-4 (2011).
Argenziano M, Lambers E, Hong L, Sridhar A, Zhang M, Chalazan B, et al. Electrophysiologic Characterization of Calcium Handling in Human Induced Pluripotent Stem Cell-Derived Atrial Cardiomyocytes. Stem Cell Reports 10:1867-1878 (2018).
De Vos CB, Pisters R, Nieuwlaat R, Prins MH, Tieleman RG, Coelen R-JS, et al. Progression From Paroxysmal to Persistent Atrial Fibrillation: Clinical Correlates and Prognosis. Journal of the American College of Cardiology 55:725-731 (2010).
Devalla HD, Schwach V, Ford JW, Milnes JT, El-Haou S, Jackson C, et al. Atrial-like cardiomyocytes from human pluripotent stem cells are a robust preclinical model for assessing atrial-selective pharmacology. EMBO molecular medicine 7: 394-410. (2015).
Feng J, Wible B, Li G-R, Wang Z, & Nattel S (1997). Antisense Oligodeoxynucleotides Directed Against Kv1.5 mRNA Specifically Inhibit Ultrarapid Delayed Rectifier K+ Current in Cultured Adult Human Atrial Myocytes. Circulation Research 80: 572-579. (1997).
Giles WR, & Imaizumi Y Comparison of potassium currents in rabbit atrial and ventricular cells. The Journal of physiology 405: 123-145. (1988).
Itzhaki I, Maizels L, Huber I, Zwi-Dantsis L, Caspi O, Winterstern A, et al. Modelling the long QT syndrome with Induced pluripotent stem cells. Nature 471: 225-229. (2011).
Müller II, Melville DB, Tanwar V, Rybski WM, Mukherjee A, Shoemaker MB, et al. Functional modeling in zebrafish demonstrates that the atrial-fibrillation-associated gene GREM2 regulates cardiac laterality, cardiomyocyte differentiation and atrial rhythm. Dis Model Mech 6: 332-341. (2013).
Musunuru K, Sheikh F, Gupta RM, Houser SR, Maher KO, Milan DJ, et al. Induced Pluripotent Stem Cells for Cardiovascular Disease Modeling and Precision Medicine: A Scientific Statement From the American Heart Association. Circulation Genomic and precision medicine 11: e000043. (2018).
Oikonomopoulos A, Kitani T, & Wu JC Pluripotent Stem Cell-Derived Cardiomyocytes as a Platform for Cell Therapy Applications: Progress and Hurdles for Clinical Translation. Molecular Therapy 26: 1624-1634. (2018a).
Oikonomopoulos A, Kitani T, & Wu JC Pluripotent Stem Cell-Derived Cardiomyocytes as a Platform for Cell Therapy Applications: Progress and Hurdles for Clinical Translation. Mol Ther 26: 1624-1634. (2018b).
Olson S, Wang MG, Carafoli E, Strehler EE, & McBride OW Localization of two genes encoding plasma membrane Ca2(+)-transporting ATPases to human chromosomes 1q25-32 and 12q21-23. Genomics 9: 629-641. (1991).
Sakuntabhai A, Ruiz-Perez V, Carter S, Jacobsen N, Burge S, Monk S, et al. Mutations in ATP2A2, encoding a Ca2+ pump, cause Darier disease. Nat Genet 21: 271-277. (1999).
Smyrnias I, Mair W, Harzheim D, Walker SA, Roderick HL, & Bootman MD Comparison of the T-tubule system in adult rat ventricular and atrial myocytes, and its role in excitation-contraction coupling and inotropic stimulation. Cell Calcium 47: 210-223. (2010).
Wann LS, Curtis AB, January CT, Ellenbogen KA, Lowe JE, Estes Nam, III, et al. ACCF/AHA/HRS Focused Update on the Management of Patients With Atrial Fibrillation (Updating the 2006 Guideline): A Report of the American College of Cardiology Foundation/American Heart Association Task Force on Practice Guidelines. Circulation 123: 104-123. (2011).
Yazawa M, Hsueh B, Jia X, Pasca AM, Bernstein JA, Hallmayer J, et al. Using iPS cells to investigate cardiac phenotypes in patients with Timothy Syndrome. Nature 471: 230-234. (2011).
Zhang Y-H, Wu H-J, Che H, Sun H-Y, Cheng L-C, Li X, et al. Functional transient receptor potential canonical type 1 channels in human atrial myocytes. Pflügers Archiv—European Journal of Physiology 465: 1439-1449. (2013).
Hashimshony et al., 2016.
Cathelijne W. van den Berg et al.Differentiation of Human Pluripotent Stem Cells to Cardiomyocytes Under Defined Conditions. (Methods Mol Biol. 2016;1353:163-80. doi: 10.1007/7651_2014_178).
Sze Ying Ng et al. Differential gene expressions in atrial and ventricular myocytes: insights into the road of applying embryonic stem cell-derived cardiomyocytes for future therapies. (Am J Physiol Cell Physiol. Dec. 2010;299(6): C1234-49. doi: 10.1152/ajpcell.00402.2009. Epub Sep. 15, 2010).
Takahashi, Tanabe et al. 2007.
Brittsan and Kranias Phospholamban and cardiac contractile function J Mol Cell Cardiol 32, 2131-2139 (2000).

* cited by examiner

Figure 2E(ii)
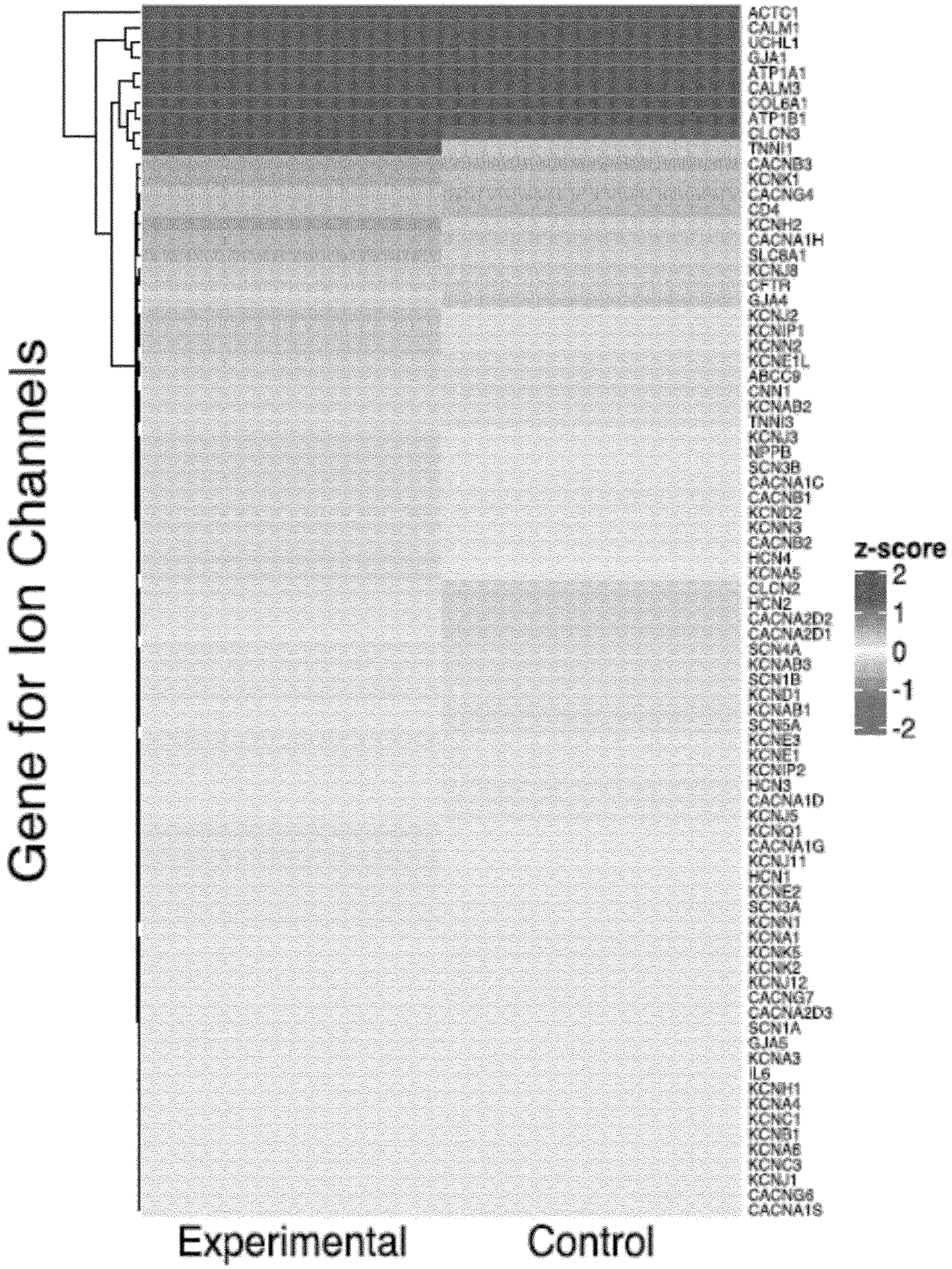

Figure 2F(ii)
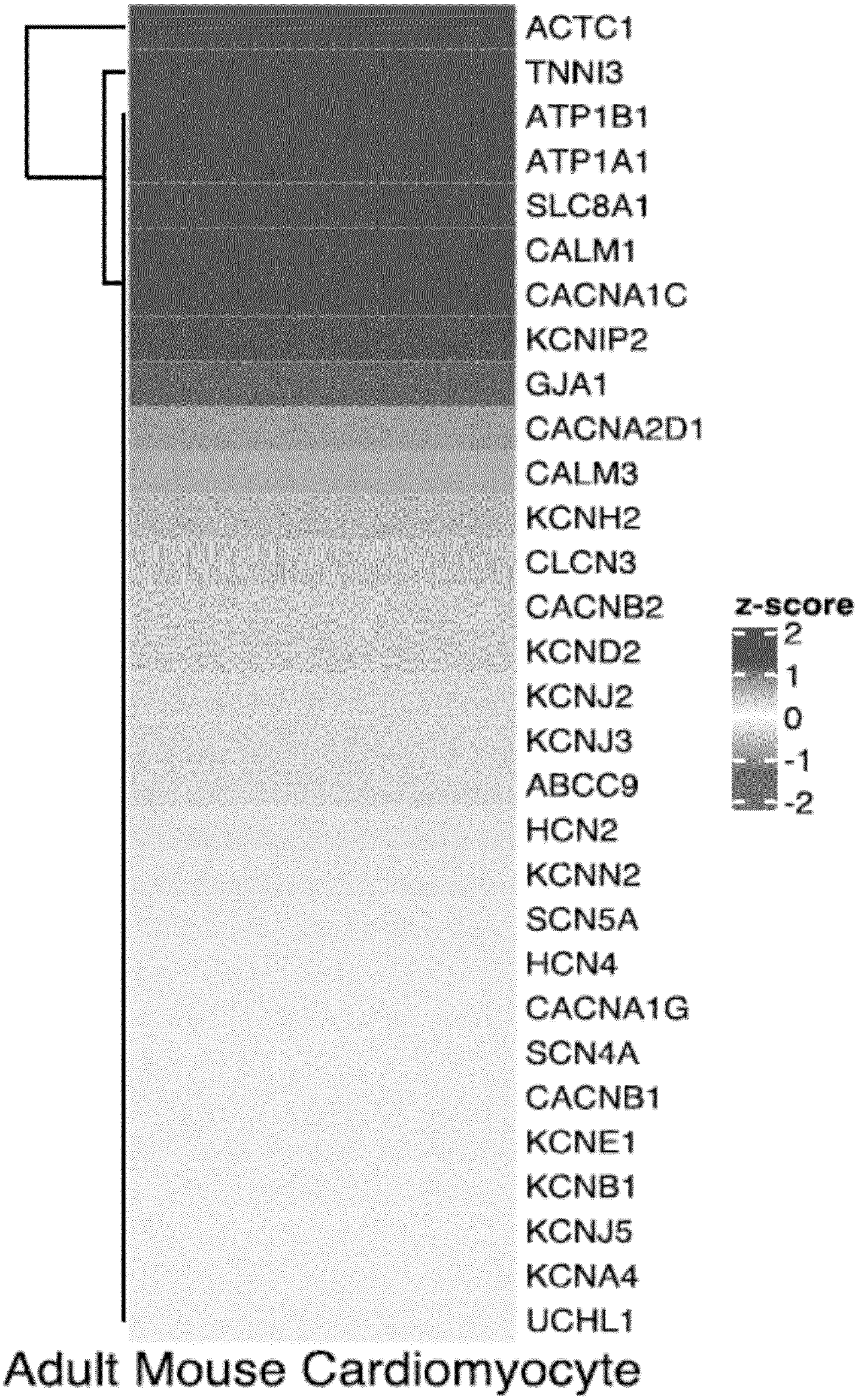
Adult Mouse Cardiomyocyte

Figure 2G(ii)
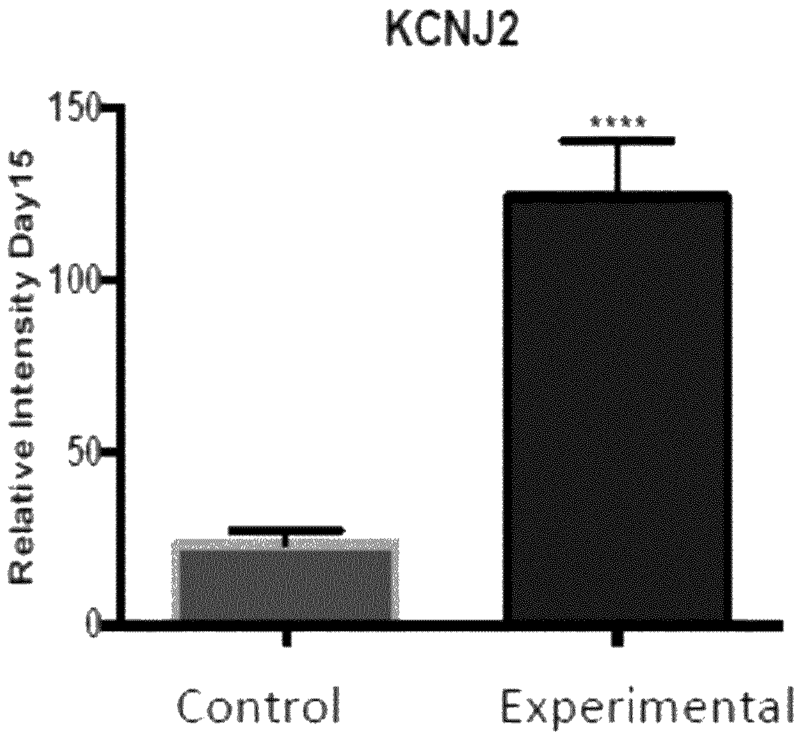

Figure 2G(iii)
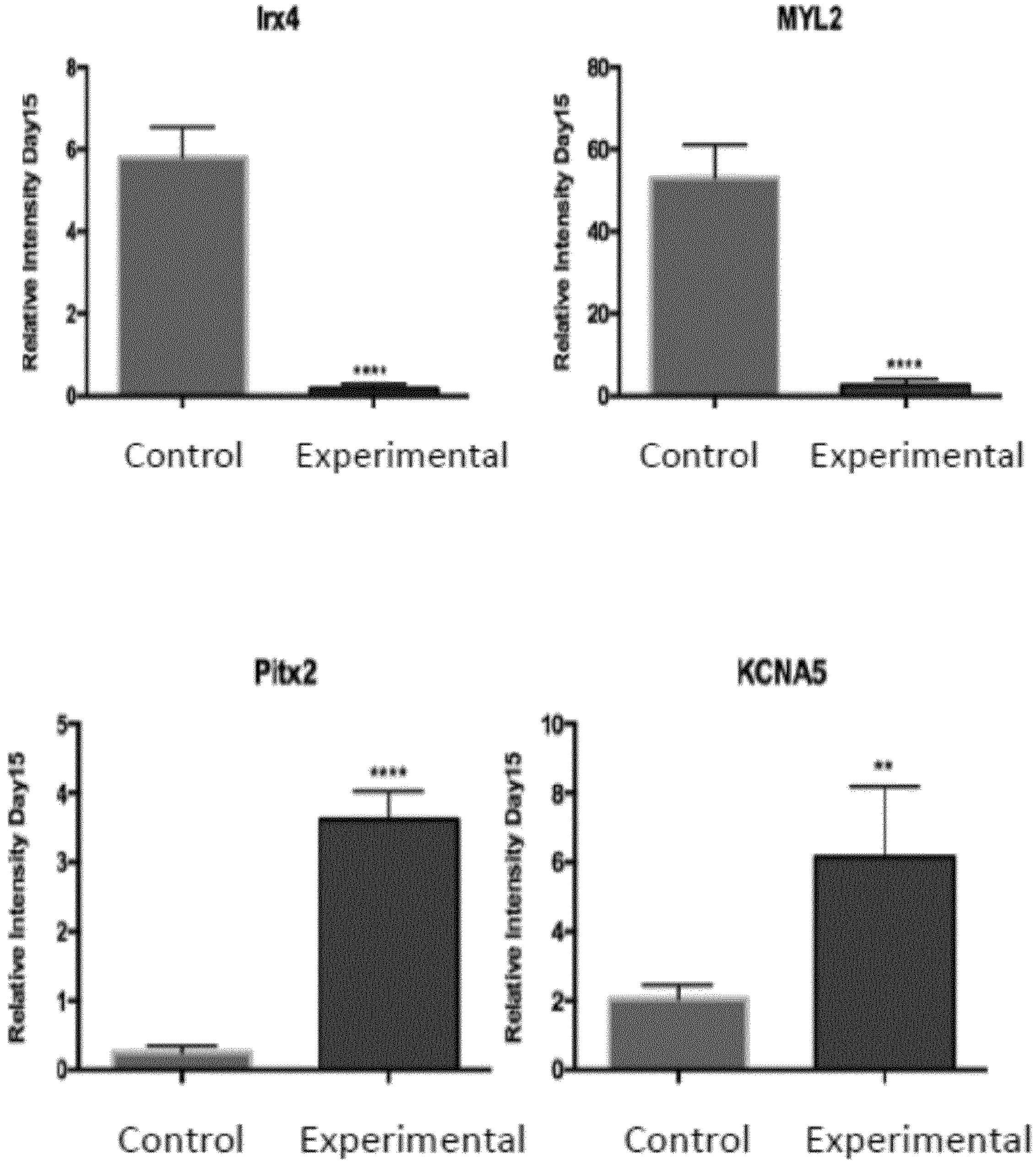

Figure 4A(ii)

Figure 4A(iii)
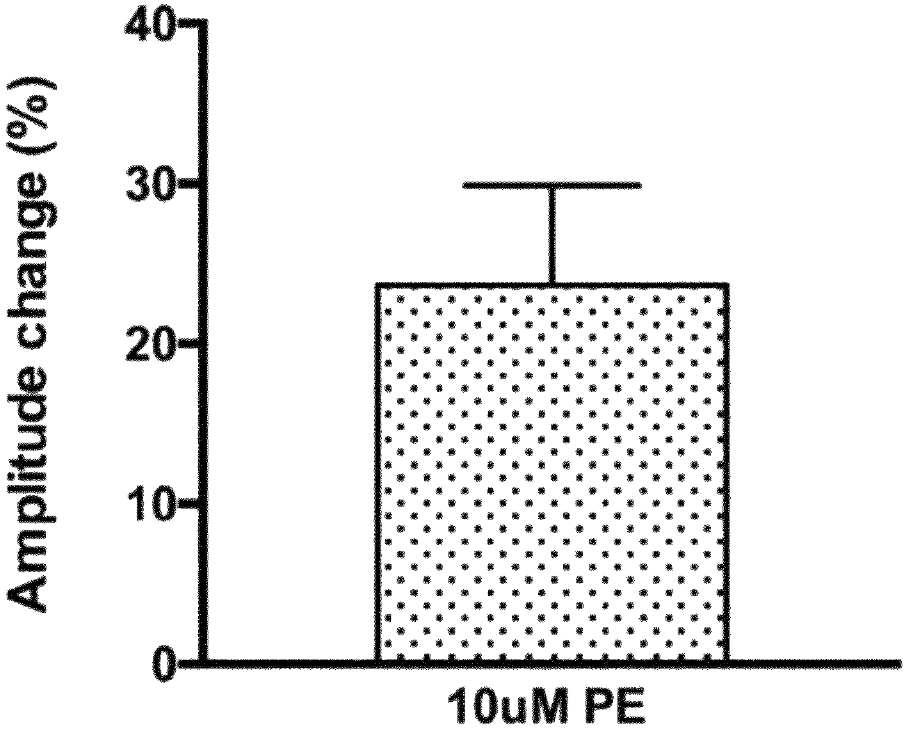
Figure 4B(i)
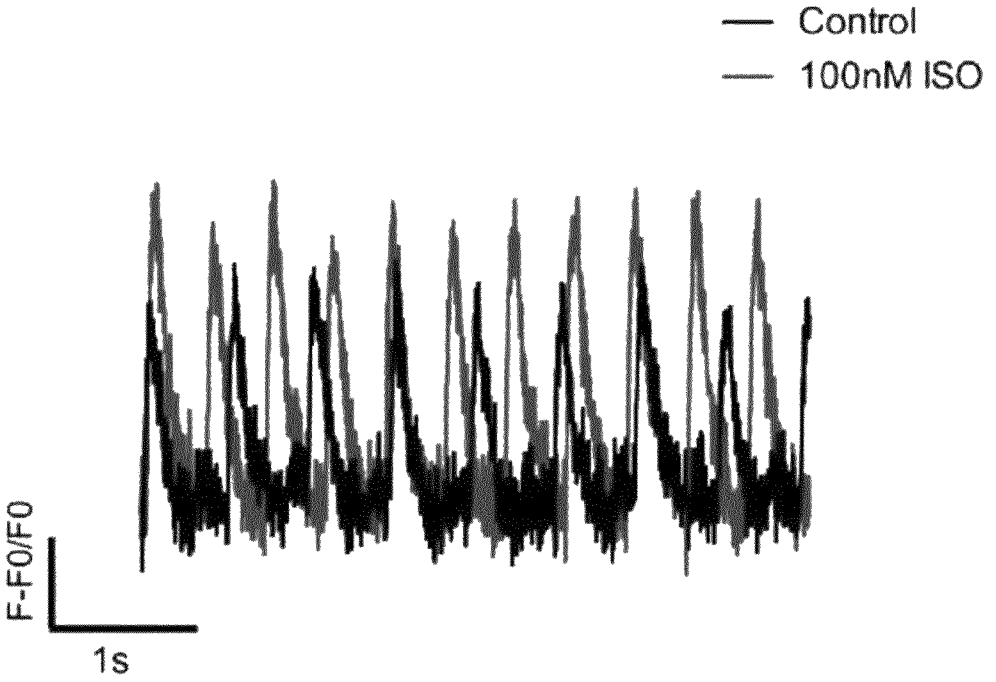

Figure 4B(ii)
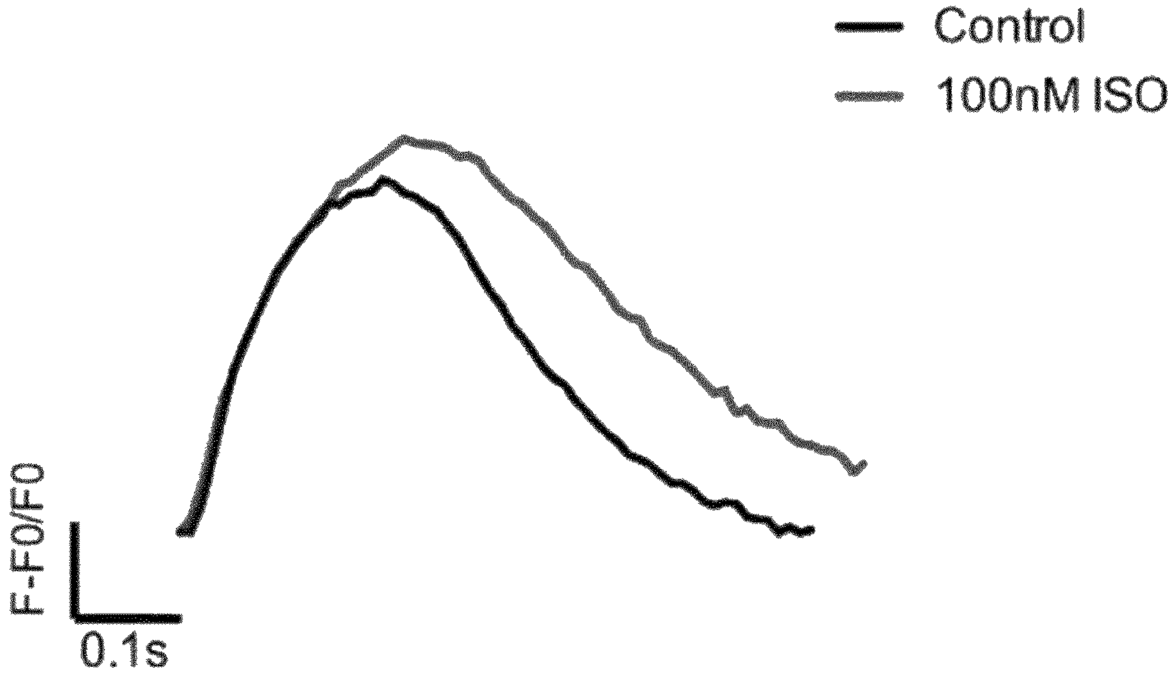
Figure 4B(iii)
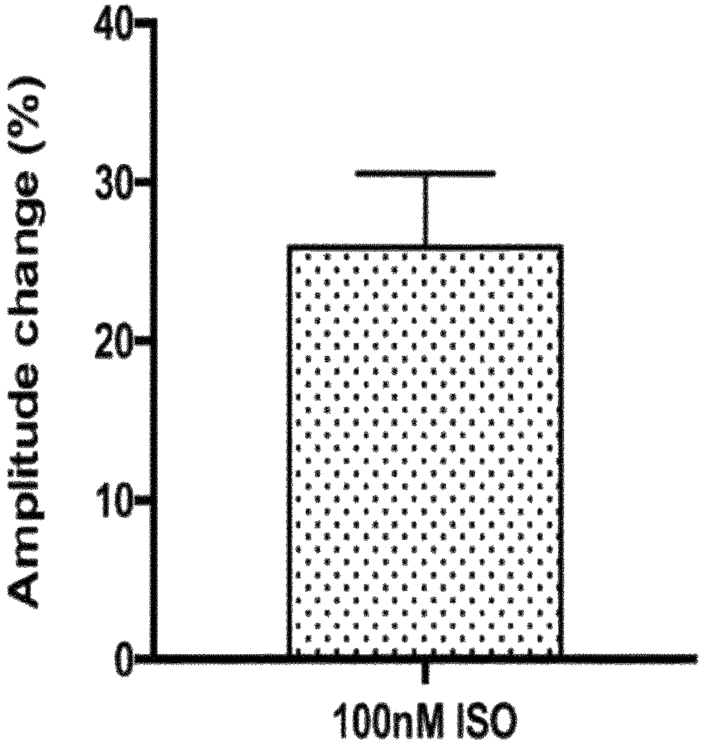

Figure 4C(ii)

Figure 4C(iii)
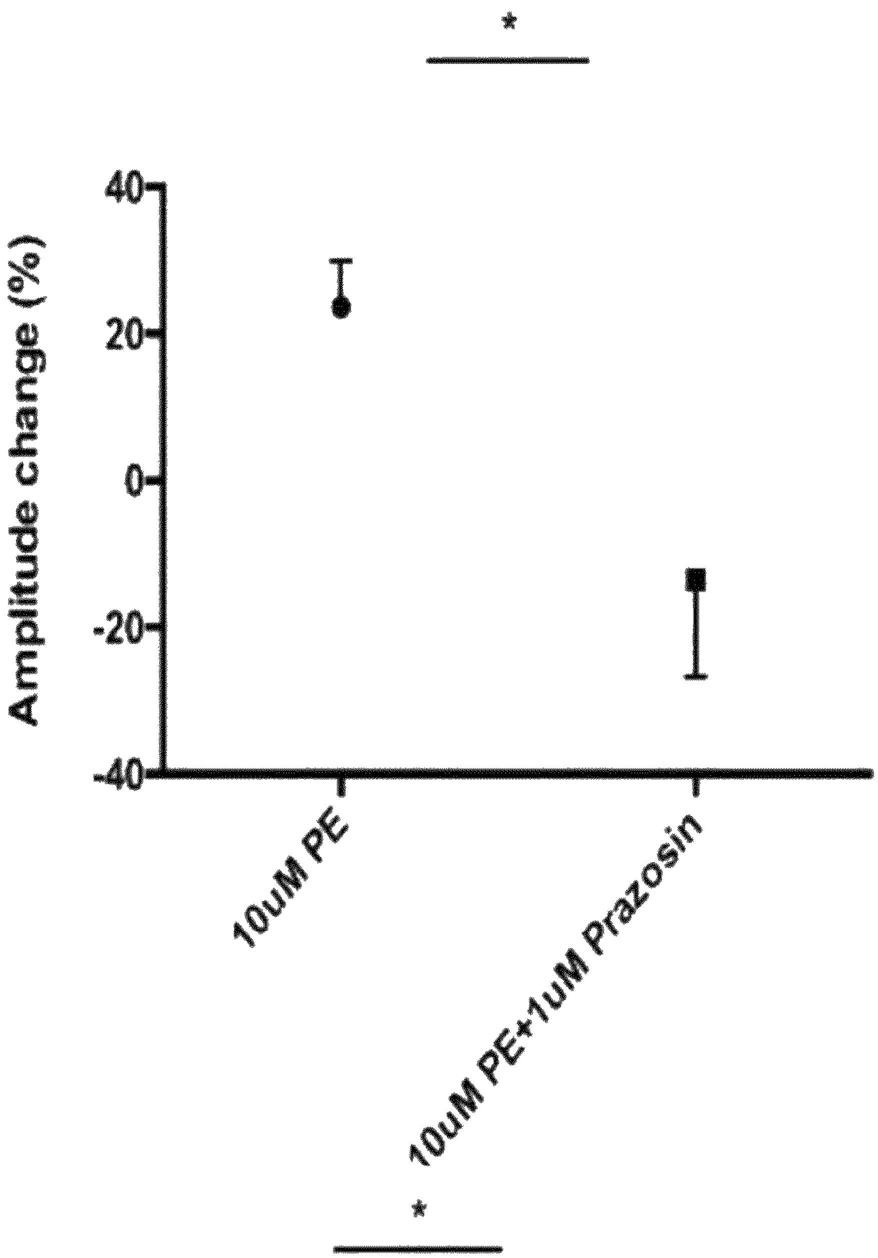

Figure 4D(ii)

Figure 4D(iii)
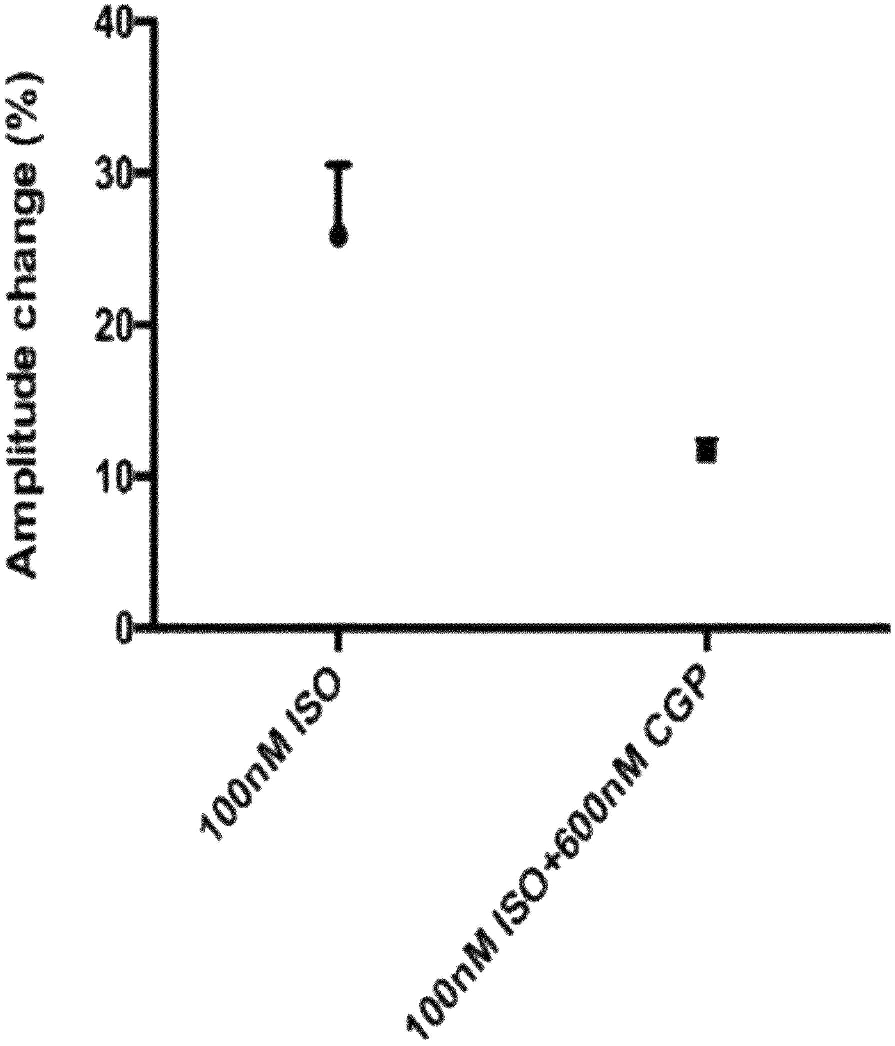

```
                     SEQUENCE LISTING


<160> NUMBER OF SEQ ID NOS: 1

<210> SEQ ID NO 1
<211> LENGTH: 168
<212> TYPE: PRT
<213> ORGANISM: Homo sapiens

<400> SEQUENCE: 1

Met Phe Trp Lys Leu Ser Leu Ser Leu Phe Leu Val Ala Val Leu Val
1               5                   10                  15

Lys Val Ala Glu Ala Arg Lys Asn Arg Pro Ala Gly Ala Ile Pro Ser
            20                  25                  30

Pro Tyr Lys Asp Gly Ser Ser Asn Asn Ser Glu Arg Trp Gln His Gln
        35                  40                  45

Ile Lys Glu Val Leu Ala Ser Ser Gln Glu Ala Leu Val Val Thr Glu
    50                  55                  60

Arg Lys Tyr Leu Lys Ser Asp Trp Cys Lys Thr Gln Pro Leu Arg Gln
65                  70                  75                  80
```

-continued

```
Thr Val Ser Glu Glu Gly Cys Arg Ser Arg Thr Ile Leu Asn Arg Phe
                85                  90                  95

Cys Tyr Gly Gln Cys Asn Ser Phe Tyr Ile Pro Arg His Val Lys Lys
            100                 105                 110

Glu Glu Glu Ser Phe Gln Ser Cys Ala Phe Cys Lys Pro Gln Arg Val
        115                 120                 125

Thr Ser Val Leu Val Glu Leu Glu Cys Pro Gly Leu Asp Pro Pro Phe
    130                 135                 140

Arg Leu Lys Lys Ile Gln Lys Val Lys Gln Cys Arg Cys Met Ser Val
145                 150                 155                 160

Asn Leu Ser Asp Ser Asp Lys Gln
                165
```

PROCESS FOR PRODUCING CARDIOMYOCYTES

CROSS-REFERENCE TO RELATED APPLICATIONS

This application is the National Stage of International Application No. PCT/EP2021/051297, filed Jan. 21, 2021, which claims priority to GB 2000903.1, filed Jan. 22, 2020, which are entirely incorporated herein by reference.

The present invention relates to a process for producing a population of cells which comprises mature atrial cardiomyocytes. The process comprises the step of treating iPS cells according to a treatment regimen which comprises contacting the iPS cells with Gremlin2 and retinoic acid, such that at least a portion of the iPS cells differentiate into mature atrial cardiomyocytes.

The invention also provides a purified population of mature atrial cardiomyocytes obtained by or obtainable by a process of the invention; and the use of such cells in drug screening or cell-replacement therapy.

Atrial fibrillation (AF) is the most frequently encountered arrhythmia in clinical practice and represents a significant disease burden worldwide, with a high prevalence and ability to cause morbidity and mortality in the population, particularly in the elderly (Wann et al., 2011). Current treatments of atrial fibrillation have major limitations including limited efficacy and significant adverse effect liability. These limitations have inspired substantial efforts concerning mechanistic research and innovative approaches for the development of new therapies, such as tailoring treatment to the underlying pathophysiology of atrial fibrillation (de Vos et al., 2010). For achieving such a goal, suitable model systems close to human tissue are required.

In recent years, human induced-pluripotent stem cells (iPSCs) have emerged as an alternative in vitro model system to the use of animal species for human disease mechanistic research and the development of new medications. Numerous disease-specific iPSC lines have been produced for modelling congenital cardiac arrhythmia syndromes including heritable atrial fibrillation (e.g. Itzhaki et al., 2011; Musunuru et al., 2018; Itzhaki et al., 2011; Musunuru et al., 2018; and Yazawa et al., 2011).

Although iPSCs hold great promise for heart disease research and treatment, there are several obvious obstacles to be overcome. For instance, cardiogenic differentiation of iPSCs by existing protocols often produce a heterogeneous mixture of cardiomyocytes (CMs) of different subtypes and primarily ventricular cardiomyocytes (Oikonomopoulos, Kitani & Wu, 2018a). More importantly, a major problem is the maturation of the hiPSC-cardiomyocytes, since these cells frequently display developmentally-immature characteristics which are analogous to fetal cardiomyocytes (Oikonomopoulos, Kitani & Wu, 2018a; Oikonomopoulos, Kitani & Wu, 2018b). The immaturity of hiPSC-cardiomyocytes makes them less suitable models for studying most heart diseases that occur in adulthood, and also diminishes the suitability of such models for drug screening.

Recently, two groups have reported the generation of hiPSC-derived atrial cardiomyocytes (HiPSC_AMs) by using retinoic acid (RA) guided differentiating protocols (Argenziano et al., 2018) (Cyganek et al., 2018)); such an RA-guided differentiating approach was also used in generating human embryonic stem cell (hESC)-derived atrial myocytes previously (Devalla et al., 2015)). These hiPSC-derived atrial cardiomyocytes showed enhanced expression of atrium-specific genes, but reduced expression of ventricle-specific genes. However, they are still not close to mature cells from the view of electrophysiological characteristics: for example, such cells frequently lack a stable resting potential and when there is a stable resting potential, the level is substantially more positive than that observed in the adult phenotype.

The inventors have now found an approach that is able to generate human iPSC-derived atrial cardiomyocytes showing mature characteristics. The new process is based on the use of a combination of RA and Gremlin 2, preferably with a specific time window of the treatment.

Gremlin 2 is key signalling molecule that is involved in cardiac development and atrial-specific differentiation (Müller et al., 2013; Tanwar et al., 2014). Using the RA/Gremlin 2 differentiating protocol, we observed a high proportion of elongated cells, some of which showed a remarkable adult atrial myocyte morphology. Atrial-type action potentials were recorded following electrical stimulation of quiescent cells with an atrial-like morphology; and in general these hiPSC-atrial cardiomyocytes possessed remarkable responses to adrenergic stimulation. These hiPSC-atrial cardiomyocytes show a transcriptomic profile with higher level of expression of several atrial-specific transcripts including NPPA, Myl7, KCNJ4, KCNJ5 and Kv1.5 compared to that of a control group treated with a standard cardiomyocyte-differentiation protocol.

Thus this new process provides an approach for differentiating mature human atrial cardiomyocytes from iPS cells that is likely to be valuable for atrial cardiomyocyte disease modelling and drug discovery.

It is an object of the invention to provide a process for producing a population of mature atrial cardiomyocytes.

In another object of the invention to provide a population of mature atrial cardiomyocytes obtained by or obtainable by a process of the invention. Such cells may be used in drug screening or cell-replacement therapy.

In one embodiment, the invention provides a process for producing a population of cells which comprises mature atrial cardiomyocytes, the process comprising the step:

(a) treating a first population of cells according to a treatment regimen, wherein the first population of cells comprises iPS cells, and wherein the treatment regimen comprises contacting the first population of cells with Gremlin2 and retinoic acid, such that at least a portion of the iPS cells in the first population of cells differentiate into mature atrial cardiomyocytes, thereby producing a second population of cells which comprises mature atrial cardiomyocytes.

Preferably, the process additionally comprises the step: (b) isolating and/or purifying a portion or all of the mature atrial cardiomyocytes from the second population of cells.

In another embodiment, the invention provides a population of cells which comprises mature atrial cardiomyocytes obtained by or obtainable by a process of the invention.

The invention also provides a purified population of mature atrial cardiomyocytes of the invention, preferably a population which is obtained or obtainable by a process of the invention.

In yet another embodiment, the invention provides the use of a purified population of mature atrial cardiomyocytes of the invention in drug screening or cell-replacement therapy.

The process of the invention involves the use of iPS cells. The term “iPS” cells refers to “induced pluripotent stem” cells. Induced pluripotent stem cells (also known iPSCs) are a type of pluripotent stem cell that can be generated directly from adult cells. The iPSC technology was pioneered by Shinya Yamanaka's lab in Kyoto, Japan, who showed in 2006 that the introduction of four specific genes (named Myc, Oct3/4, Sox2 and Klf4) encoding transcription factors could convert adult cells into pluripotent stem cells (Takahashi K, Yamanaka S (August 2006). "Induction of pluripotent stem cells from mouse embryonic and adult fibroblast cultures by defined factors". Cell. 126 (4): 663-76).

Preferably, the iPS cells are mammalian cells, e.g. human, mouse, rat, monkey, pig, cow, horse or goat cells. Most preferably, the iPS cells are human cells.

The iPS cells may be derived from any suitable cells including any somatic cell type. In one embodiment, the iPS cells are derived from umbilical cord blood cells. More preferably, the iPS cells are derived from umbilical cord blood $CD34^+$ progenitor cells.

In another embodiment, the iPS cells are derived from peripheral blood mononuclear cells (PBMCs) or from fibroblasts.

In some embodiments, the iPS cells are derived from a disease-specific cell line. Numerous disease-specific iPS cell lines have been produced for modelling congenital cardiac arrhythmia syndromes including heritable atrial fibrillation (e.g. Itzhaki et al., 2011; Musunuru et al., 2018; Itzhaki et al., 2011; Musunuru et al., 2018; and Yazawa et al., 2011).

iPS cells are typically derived by introducing products of specific sets of pluripotency-associated genes, or "reprogramming factors", into a given cell type. The original set of reprogramming factors (also dubbed Yamanaka factors) are the transcription factors Oct4 (Pou5f1), Sox2, cMyc, and Klf4. While this combination is most conventional in producing iPSs, each of the factors can be functionally replaced by related transcription factors, miRNAs, small molecules, or even non-related genes such as lineage specifiers (Guo X L, Chen J S (2015). "Research on induced pluripotent stem cells and the application in ocular tissues". International Journal of Ophthalmology. 8 (4): 818-25).

Methods of producing iPS cells are now well known the art (e.g. Shi Y, Inoue H, Wu J C, Yamanaka S. "Induced pluripotent stem cell technology: a decade of progress". Nat Rev Drug Discov. 2017 February; 16(2):115-130. doi: 10.1038/nrd.2016.245. Epub 2016 Dec. 16; Sayed N, Liu C, Wu J C. "Translation of Human-Induced Pluripotent Stem Cells: From Clinical Trial in a Dish to Precision Medicine". J Am Coll Cardiol. 2016 May 10; 67(18):2161-2176. doi: 10.1016/j.jacc.2016.01.083; and Matsa E, Burridge P W, Wu J C. "Human stem cells for modeling heart disease and for drug discovery", Sci Transl Med. 2014 Jun. 4; 6(239): 239ps6. doi: 10.1126/scitranslmed.3008921).

The generation of iPS cells is dependent on the transcription factors used for the induction.

Oct-3/4 and certain products of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (c-myc, L-myc, and N-myc), Nanog, and LIN28, have been identified to increase the induction efficiency.

Oct-3/4 (Pou5f1) Oct-3/4 is one of the family of octamer ("Oct") transcription factors, and plays a crucial role in maintaining pluripotency. The absence of Oct-3/4 in Oct-3/4+ cells, such as blastomeres and embryonic stem cells, leads to spontaneous trophoblast differentiation, and presence of Oct-3/4 thus gives rise to the pluripotency and differentiation potential of embryonic stem cells. Various other genes in the "Oct" family, including Oct-3/4's close relatives, Oct1 and Oct6, fail to elicit induction, thus demonstrating the exclusiveness of Oct-3/4 to the induction process. However a team headed by Hans Schöler (who discovered the Oct4 gene back in 1989) showed that Oct4 overexpression during reprogramming causes epigenetic changes deteriorating the quality of iPSCs. Comparing to OSKM (Oct4, Sox2, Klf4 and c-Myc) new SKM (Sox2, Klf4 and c-Myc) reprogramming generates iPSCs with developmental potential equivalent to embryonic stem cell, as determined by their ability to generate all-iPSC mice through tetraploid embryo complementation.

Sox family: The Sox family of transcription factors is associated with maintaining pluripotency similar to Oct-3/4, although it is associated with multipotent and unipotent stem cells in contrast with Oct-3/4, which is exclusively expressed in pluripotent stem cells. While Sox2 was the initial gene used for induction by Yamanaka et al., Jaenisch et al. (Hockemeyer D, Jaenisch R (May 2016). "Induced Pluripotent Stem Cells Meet Genome Editing". Cell Stem Cell. 18 (5): 573-86) and Thomson et al. (Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A (December 2007). "Induced pluripotent stem cell lines derived from human somatic cells". Science. 318 (5858): 1917-20) other transcription factors in the Sox family have been found to work as well in the induction process. Sox1 yields iPS cells with a similar efficiency as Sox2, and genes Sox3, Sox15, and Sox18 also generate PS cells, although with decreased efficiency.

Klf family: Klf4 of the Klf family of transcription factors was initially identified by Yamanaka et al. and confirmed by Jaenisch et al. as a factor for the generation of mouse iPS cells and was demonstrated by Yamanaka et al. as a factor for generation of human iPS cells. However, Thomson et al. reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

Myc family: The Myc family of transcription factors are proto-oncogenes implicated in cancer. Yamanaka et al. and Jaenisch et al. demonstrated that c-myc is a factor implicated in the generation of mouse iPS cells and Yamanaka et al. demonstrated it was a factor implicated in the generation of human iPS cells.

Nanog: In embryonic stem cells, Nanog, along with Oct-3/4 and Sox2, is reported to be necessary for promoting pluripotency.

LIN28: LIN28 is an mRNA binding protein expressed in embryonic stem cells and embryonic carcinoma cells associated with differentiation and proliferation. Thomson et al. demonstrated that LIN28 is a factor in iPSC generation in combination with OCT4, SOX2, and NANOG.

Glis1: Glis1 is transcription factor that can be used with Oct-3/4, Sox2 and Klf4 to induce pluripotency. It poses numerous advantages when used instead of C-myc.

In one preferred method, cord blood-derived CD34+ progenitor cells are reprogrammed using OCT4, Sox2, Myc, Klf4, Nanog, SV40LT and Lin28 antigen. Such cells may be purchased from Gibco® Life Technology (Carlsbad, USA).

iPS cell lines may be characterized by numerous methods including immunostaining, qPCR, tri-lineage differentiation, teratoma assay and/or karyotyping.

Preferably, the iPS cells are a homogeneous population or a population of substantially homogeneous iPS cells. In some embodiments, the first population consists of or consists substantially of a population of the desired iPS cells. More preferably, at least 70%, 80%, 90% or 95% of the first population of cells are iPS cells. The first population of cells comprises no or substantially no mature atrial cardiomyocytes.

The iPS cells are cultured in an appropriate composition, e.g. a suitable iPS cell culture medium. Preferably, the iPS cells are regularly passaged upon reaching an appropriate level of confluency (e.g. 60-80%, preferably 70%). Preferably, the iPS cells are passaged every 3-5, preferably 4 days.

Preferably, at the start of the treatment regimen, all or substantially all of the iPS cells are dissociated into single cells. In some embodiments, the iPS cells are full separated, individual iPS cells, which are preferably evenly distributed.

Preferably, the treatment regimen is started by contacting the first population of cells with a cardiac cell differentiation medium. As used herein, cardiac cell differentiation media are tissue culture media which are suitable for culturing iPS cells and cardiomyocytes. In particular, they are suitable for promoting the differentiation of iPS cells to cardiac cells. The cardiac cell differentiation media are preferably based on a standard tissue culture medium, e.g. RPMI 1640. One example of such a medium is CDM3 (Burridge et al. “Chemically defined generation of human cardiomyocytes”. Nat Methods. 2014, 11:855-860), a chemically-defined medium consisting of RPMI 1640, rice-derived recombinant human albumin, and L-ascorbic acid 2-phosphate.

The first population of cells are preferably contacted with a number of different cardiac cell differentiation media. In particular, the use of the first and second cardiac cell differentiation media (as defined herein) help to promote the differentiation of iPS cells to cardiac cells.

It is known that differentiation towards cardiomyocyte cell lineages may be induced using small molecules to modulate the WNT signalling pathway, first with a GSK3B inhibitor to potentiate WNT signalling and then 2 days later with a WNT inhibitor to attenuate WNT signalling (e.g. “Chemically Defined Culture and Cardiomyocyte Differentiation of Human Pluripotent Stem Cells” Burridge et al., Curr. Protoc. Hum. Genet. 2015; 87: 21.3.1-21.3.15; Burridge et al. “Chemically defined generation of human cardiomyocytes”, Nat Methods. 2014; 11:855-860; Gonzalez R, et al. “Stepwise chemically induced cardiomyocyte specification of human embryonic stem cells”. Angew Chem Int Ed Engl. 2011; 50:11181-11185; and Lian X, et al. “Robust cardiomyocyte differentiation from human pluripotent stem cells via temporal modulation of canonical Wnt signaling”. Proc. Natl. Acad. Sci. USA. 2012; 109:E1848-1857).

As used herein, the term “first cardiac cell differentiation medium” refers to a cardiac cell differentiation medium which comprise a moiety which is capable of potentiating the WNT signalling pathway. Preferably, this moiety is a GSK3B inhibitor.

Examples of GSK3B inhibitors include lithium ions, valproic acid, iodotubercidin, Naproxen, Cromolyn, Famotidine, Curcumin, Olanzapine, CHIR99021 and pyrimidine derivatives. Preferably, the GSK3B inhibitor is CHIR99021.

The first cardiac cell differentiation medium does not comprise a WNT inhibitor.

A cell-permeable, potent and selective inhibitor of Rho-associated, coiled-coil containing protein kinase (ROCK) may be added to the first cardiac cell differentiation medium (e.g. Y-27632, Stemcell Technologies).

As used herein, the term “second cardiac cell differentiation medium” refers to a cardiac cell differentiation medium which comprise a moiety which is capable of attenuating the WNT signalling pathway. (See Willems E, et al. (August 2011). “Small-molecule inhibitors of the Wnt pathway potently promote cardiomyocytes from human embryonic stem cell-derived mesoderm”. Circulation Research. 109 (4): 360-4; and Burridge P W, et al. (August 2014). “Chemically defined generation of human cardiomyocytes”. Nature Methods. 11 (8): 855-60).

Preferably, this moiety is a WNT inhibitor. Examples of WNT inhibitors include Dickkopf (Dkk), Wnt inhibitory factor 1 (WIF-1), secreted Frizzled-related proteins (SFRP), Cerberus, Frzb, Wise, SOST, Naked cuticle, IWR-1, IWP-2 and Wnt-C59. Preferably, the WNT inhibitor is Wnt-C59.

A cell-permeable, potent and selective inhibitor of Rho-associated, coiled-coil containing protein kinase (ROCK) may be added to the second cardiac cell differentiation medium (e.g. Y-27632, Stemcell Technologies).

The second cardiac cell differentiation medium does not comprise a moiety which is capable of potentiating the WNT signalling pathway.

The treatment regimen comprises the step of contacting the first population of cells with Gremlin2 and retinoic acid.

The Gremlin2 gene encodes a member of the BMP (bone morphogenic protein) antagonist family. Like BMPs, BMP antagonists contain cysteine knots and typically form homo- and heterodimers. The CAN (cerberus and dan) subfamily of BMP antagonists, to which this gene belongs, is characterized by a C-terminal cysteine knot with an eight-membered ring.

Gremlin2 is also known as Gremlin 2, DAN Family BMP Antagonist; Protein Related To DAN And Cerberus; Cysteine Knot Superfamily 1, BMP Antagonist; DAN Domain Family Member; Gremlin-2; CKTSF1B2; DAND3; PRDC; Gremlin 2, Cysteine Knot Superfamily, Homolog; Gremlin 2; and STHAG9. Gremlin2 protein may be obtained from R&D Systems (USA).

Preferably, the Gremlin2 protein has the sequence given herein in SEQ ID NO: 1, or a variant thereof having at least 80%, 90% or 95% sequence identity thereto and which inhibits BMP-4-induced activity (e.g. in MC3T3-E1 mouse pre-osteoblast cells), preferably with an $ED_{50}$ of 0.03-0.12 μg/mL. Unless the context requires otherwise, references herein to Gremlin2 refer to the Gremlin2 protein.

Retinoic acid is a metabolite of vitamin A1 (all-trans-retinol) that mediates the functions of vitamin A1 required for growth and development.

All-trans-retinoic acid (ATRA) is the major occurring retinoic acid, while isomers like 13-cis- and 9-cis-retinoic acid are also present in much lower levels.

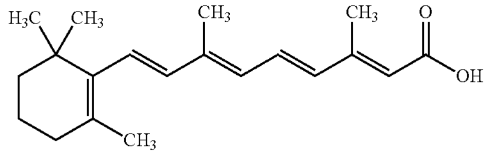 [SMILES: CC1=C(/C=C/C(C)=C/C=C/C(C)=C/C(=O)O)C(C)(C)CCC1]

Retinoic acid may be obtained from Sigma-Aldrich (UK) (e.g. catalogue no. R2625). Preferably, the retinoic acid is all-trans-retinoic acid (ATRA) or substantially all-trans-retinoic acid (ATRA).

In some embodiments, the treatment regimen comprises contacting the first population of cells with effective amounts of Gremlin2 and retinoic acid, such that at least a portion of the iPS cells in the first population of cells differentiate into mature atrial cardiomyocytes.

In other embodiments, the treatment regimen comprises contacting the first population of cells with amounts of Gremlin2 and retinoic acid at appropriate times and durations such that at least a portion of the iPS cells in the first population of cells differentiate into mature atrial cardiomyocytes.

In yet other embodiments, the treatment regimen comprises contacting the first population of cells with effective amounts of Gremlin2 and retinoic acid at appropriate times and durations such that at least a portion of the iPS cells in the first population of cells differentiate into mature atrial cardiomyocytes.

In some preferred embodiments, the iPS cells are first contacted with Gremlin2 and then contacted with retinoic acid. Preferably, the iPS cells are first contacted with Gremlin2 for 1-3 days, preferably for about 2 days, before they are contacted with retinoic acid.

As used herein, reference to days refer to a 24 hour time period +/−6 hours.

Preferably, at the start of the treatment regimen, the first population of cells are placed in a cardiac cell differentiation medium. The day that this is done may be defined as Day 0.

Preferably, the first population of cells are first cultured in the first cardiac cell differentiation medium (starting on Day 0). Preferably, the first population of cells are first cultured in the first cardiac cell differentiation medium for 1-3 days, more preferably 1.5-2.5 days, and most preferably for about 2 days.

Preferably, the first population of cells are then cultured in the second cardiac cell differentiation medium. Preferably, the cardiac cell differentiation medium is changed at this time.

Preferably, the first population of cells are then cultured in the second cardiac cell differentiation medium for 1-3 days, more preferably 1.5-2.5 days, and most preferably for about 2 days.

The first population of cells are then cultured in a cardiac cell differentiation medium which comprises Gremlin2. This cardiac cell differentiation medium preferably does not comprise a potentiator or inhibitor of the WNT signalling pathway. Preferably, the cardiac cell differentiation medium is changed at this time.

The amount of Gremlin2 which is present in this cardiac cell differentiation medium is an amount which is effective, in combination with retinoic acid, for at least a portion of the iPS cells to differentiate into mature atrial cardiomyocytes.

Preferably, Gremlin2 is present in the cardiac cell differentiation medium at a final concentration of 0.1-10 μg/ml, more preferably 1-5 μg/ml.

Gremlin2 is preferably first present in the cardiac cell differentiation medium between Day 2 to Day 4, more preferably at Day 4.

Preferably, Gremlin2 is present in the cardiac cell differentiation medium for 1, 2, 3, 4, 5, 6, 7 or 8 days, more preferably for 2-4 days.

Gremlin2 is most preferably present in the cardiac cell differentiation medium between Day 4 to Day 6.

Preferably, Gremlin2 is added to the cardiac cell differentiation medium every other day during its treatment window, in order to maintain the optimal dosage.

Most preferably, Gremlin2 is applied to the cardiac cell differentiation medium from Day 4 to Day 6 to maintain the optimal dosage.

Preferably, Gremlin2 is applied to the cardiac cell differentiation medium before retinoic acid is applied.

The first population of cells are then cultured in a cardiac cell differentiation medium which comprises retinoic acid. This cardiac cell differentiation medium preferably does not comprise a potentiator or inhibitor of the WNT signalling pathway.

Preferably, the cardiac cell differentiation medium is changed at this time.

The amount of retinoic acid which is present in the cardiac cell differentiation medium is an amount which is effective for at least a portion of the first population of cells to differentiate into mature atrial cardiomyocytes.

Preferably, retinoic acid is used in the cardiac cell differentiation medium at a final concentration of 0.1-10 μM, more preferably 0.5-2.0 μM, and most preferably at about 1.0 μM.

Retinoic acid is preferably present in the cardiac cell differentiation medium between Day 5 to Day 10, preferably at Day 6. Preferably, retinoic acid is present in the cardiac cell differentiation medium for 1, 2, 3, 4, 5, 6, 7 or 8 days, more preferably for 3-6 days.

Retinoic acid is most preferably present in the cardiac cell differentiation medium between Day 6 to Day 10. Preferably, retinoic acid is added to the cardiac cell differentiation medium every other day during its treatment window, in order to maintain the optimal dosage.

Most preferably, RA is first applied to the composition at Day 6, and then again at Day 8, to maintain the optimal dosage.

Thereafter, the first population of cells may be cultured in cardiac cell differentiation medium (without a potentiator or inhibitor of the WNT signalling pathway, Gremlin2 or retinoic acid). Preferably, the cardiac cell differentiation medium is changed at this time.

In a particularly-preferred embodiment of the invention, the treatment regimen comprises:

(i) culturing the first population of cells in the first cardiac cell differentiation medium between Day 0 and Day 2;

(ii) culturing the first population of cells in the second cardiac cell differentiation medium between Day 2 and Day 4;

(iii) culturing the first population of cells in cardiac cell differentiation medium comprising Gremlin2 between Day 4 and Day 6; and (iii) culturing the first population of cells in cardiac cell differentiation medium comprising retinoic acid between Day 6 and Day 10.

Preferably, the cardiac cell differentiation medium is changed between each of the above steps.

The cardiac cell differentiation medium may additionally comprise one or more components which are suitable for the culture of iPS cells. For example, the cardiac cell differentiation medium may additionally comprise a feeder-free cell culture medium which is suitable for human embryonic stem cells and/or and induced pluripotent stem cells. One example of such a medium is mTeSR™1 from Stemcell Technologies.

The invention provides a process, as defined herein, for producing a second population of cells which comprises mature atrial cardiomyocytes. The second population of cells will substantially all be differentiated cardiomyocytes. Preferably, the second population comprises no or essentially no iPS cells.

The mature atrial cardiomyocytes which are produced by a process of the invention have a phenotype which is similar to that of mature atrial cardiomyocytes which are observed in human and animal hearts. The mature atrial cardiomyocytes which are produced by a process of the invention have a single nucleus. They show a well-organised sarcomere pattern with striation (preferably wherein the average sarcomere spacing is less than 2 μm).

The mature atrial cardiomyocytes which are produced by a process of the invention may also be characterised by the expression of all of the following biomarkers: α-actinin, TNNT2 (coding for cardiac troponin A), NPPA (coding for natriuretic peptide A) and COUP-TFII (also known as nuclear family receptor 2, group F, member 2). Preferably, at least 60%, 70%, 80% or 90% of the population of mature atrial cardiomyocytes of the invention are positive for the atrial-specific COUP-TFII/NPPA. The mature atrial cardiomyocytes which are produced by a process of the invention also express RyR2 receptors, α-actininin2 and F-actin.

The mature atrial cardiomyocytes which are produced by a process of the invention may also be characterised by the expression of one or more of the following genes which are specific for atrial cardiomyocytes: MYL7, HEY1, HOXA1, SLN, MYH6, KCNH2, GATA4 and NPPA.

Genes encoding potassium channels Kv1.5 (KCNA5), and Kv11.1 (KCNH2) may also be expressed.

The mature atrial cardiomyocytes which are produced by a process of the invention are electrically quiescent, but can be stimulated to fire an action potential.

The mature atrial cardiomyocytes which are produced by a process of the invention may also be characterised by their resting membrane potential. Using a patch clamp method under a whole cell configuration, human atrial myocytes are known to have an average resting membrane potential of approximately −74 mV; the corresponding value for human ventricular cells is −81 mV. In contrast, the mature atrial cardiomyocytes which are produced by a process of the invention have an average resting membrane potential of approximately −67 mV.

Furthermore, the action potential amplitude (APA) for mature atrial cardiomyocytes which are produced by a process of the invention is approximately 99 mV; the corresponding value for human atrial cardiomyocytes is approximately 89 mV.

The second population of cells will substantially all be differentiated cardiomyocytes.

Preferably, at least 40%, 50%, 60%, 70%, 80%, 90% or 95% of the second population of cells have the characteristics of mature atrial cardiomyocytes (as defined herein).

In a further embodiment, the process additionally comprises the step: (b) isolating and/or purifying a portion or all of the mature atrial cardiomyocytes from the second population of cells. The mature atrial cardiomyocytes may be isolated by any suitable means, e.g. FACS, antibody column, etc., using one or more cell-surface specific markers for atrial cardiomyocytes.

In a further embodiment, the invention provides a population of cells which comprises both immature cardiomyocytes and mature atrial cardiomyocytes, preferably a population which is obtained or obtainable by a process of the invention.

The invention also provides a purified population of mature atrial cardiomyocytes of the invention, preferably a population which is obtained or obtainable by a process of the invention.

In a further embodiment, the invention provides a population of purified mature atrial cardiomyocytes, wherein the mature atrial cardiomyocytes have one or both of the following features:

(i) an average resting membrane potential of approximately −67 mV (using a patch clamp method under a whole cell configuration);

(ii) an action potential amplitude of approximately 99 mV.

The invention also provides a cell-line derived from a population of purified mature atrial cardiomyocytes of the invention.

In a further embodiment, the invention provides the use of a purified population of mature atrial cardiomyocytes of the invention, or a cell line obtained therefrom, in drug screening or in cell-replacement therapy.

The process of the invention is carried out in vitro or ex vivo.

The disclosure of each reference set forth herein is specifically incorporated herein by reference in its entirety.

Figure 1A:
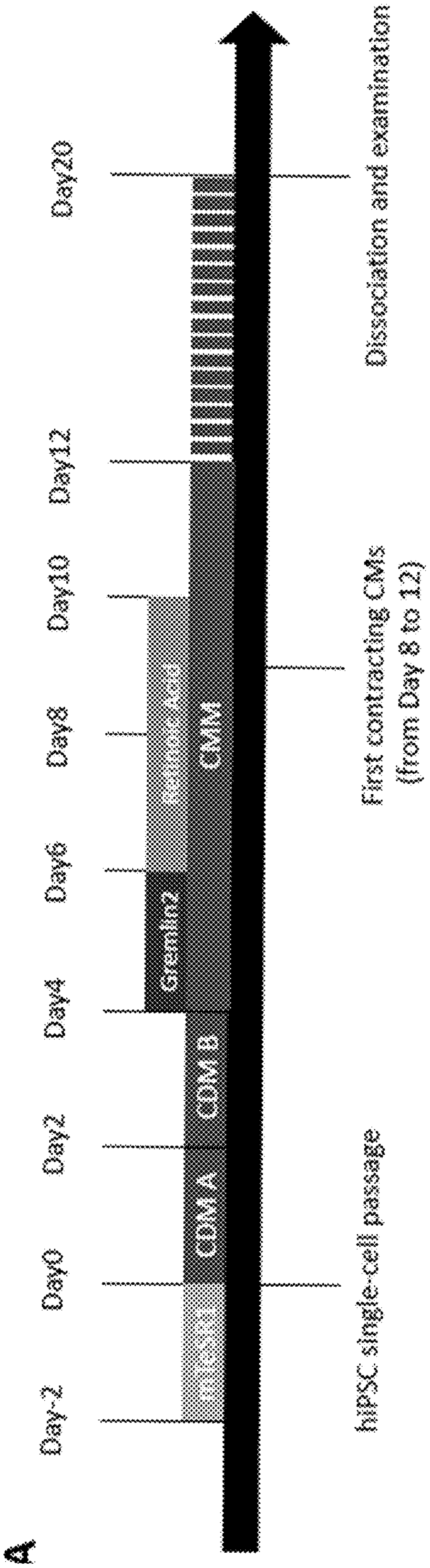
FIG. 1. Gremlin2/RA-mediated differentiation of iPSCs into atrial cardiomyocytes.

(A) Schematic of the atrial-specific differentiation protocols. Human iPSCs were dissociated into single cardiomyocytes for the differentiation experiments. Cardiac Differentiation Medium A including CHIR99021 and Cardiac Differentiation Medium B was applied to both groups. From day 4, all cardiomyocytes were maintained in cardiomyocyte maintenance medium (CMM). Gremlin 2 (1 g/ml) and retinoic acid (1.0 M) were applied to the experimental group, while control group cells were differentiated without the addition of Gremlin 2 and RA. Functional analysis was performed after day 20.

(B) Day20 hiPSC-derived cardiomyocyte showed expression of the cardiomyocyte-specific cytoskeleton markers α-actinin and TNNT in both cell populations and restricted expression of the atrial cardiomyocyte-specific markers COUP-TFII and NPPA to gremlin2/RA-treated CMs, but not the untreated counterparts.

(C) Immunofluorescence-labelling of the cytoskeleton marker α-actinin and F-actinin demonstrated an elongated and latticed cell morphology.

(D) The percentage of COUP-TFII positive cardiomyocytes reached approximately 80% in the Gremlin2/RA-treated group. A total of 94 DAPI-stained cell nuclei were identified in both treated and control groups, and then they were overlapped with COUP-TFII positive nuclei to calculate the percentage of COUP-TFII positive cells. A chi-squared test was applied, n=94, P<0.001.

FIG. 2. Single cell transcriptomic profile.

(A) t-sne plot of the scRNAseq of both groups of hIPSC-derived cardiomyocytes.

(B) Differential gene expression analysis showed many up-regulated atrial-specific genes in the experimental group; selected markers are indicated.

(C) Violin plots of individual expression of atrial (MYL7 and HEY1), ventricular (SCUBE3 and GJA1) and general cardiac genes (TNNT2 and ACTN4) at days 20.

(D) Highlight of individual cells expressing selected atrial-specific gene (HEY1, MYL7, HOXA3 and SLN) in separated t-sne plots.

(E) Heatmap of gene expression for calcium ion handling protein, adrenergic signaling and ion channels.

(F) Comparison of top 30 gene expressions for ion channels in between human iPSC-derived CMs and adult mouse cardiomyocytes.

(G) Time-lapsing qRT-PCR gene analysis of NPPA over a 20 day time course and qRT-PCR gene analysis of atrial or ventricle-specific genes on day15. Values shown are relative to housekeeping gene HPRT. n=5, SD of mean, p<0.001.

FIG. 3. Electrophysiological features of hiPSC-derived CMs on differentiation day 20.

(A) (i)&(iii) action potential track from a representative Gremlin2/RA-treated hiPSC-derived CM. (ii)&(iv) The action potential of one single beat from the representative cell.

(B) Average resting potential (RP) of seven cells from Gremlin2/RA-treated group was −66.67±5.85 mV (n=7); average action potential amplification (APA) of seven cells from Gremlin2/RA-treated group was 99.15±2.74 mV (n=7); The action potential duration at 90 and 50% repolarization ($APD_{90}$, $APD_{50}$) observed in seven experimental cells were 215±30 ms and 130±30 ms (n=7).

(C) Action potential track from a representative untreated hiPSC-derived CM.

(D) RP and APA of seven cells from untreated group; Data are presented as mean±SEM.

FIG. 4. Calcium ion transient amplitude manipulation by exogenous molecules in Gremlin2/RA treated iPSC-CMs.

(A) Calcium traces in one representative experiment before and 10 minutes after 10 uM PE treatment.

(B) Calcium traces in one representative experiment before and 10 minutes after 100 nM ISO treatment.

(C) α-adrenergic antagonist (Prazosin) abolished the effects of adrenergic stimulation by 10 uM PE. Traces were recorded 10 min after 10 uM PE treatment to 1 uM prazosin pre-treated iPSC-CMs.

(D) β-adrenergic antagonists (GCP) abolished the effects of adrenergic stimulation by 10 uM PE. Traces were recorded 10 min after 10 uM PE treatment to 600 nM GCP pre-treated iPSC-CMs. (i) Raw traces. (ii) Averaged trace. (iii) An average of increase in $Ca^{2+}$ transient amplitude in response to drug treatment. Four independent experiments were conducted for PE and examination respectively (n=4). Data are presented as mean±SEM, *P<0.05.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Materials and Methods iPSC Cell Culturing, Differentiation and Characterizations

The iPSCs lines used for the cardiomyocyte differentiation were purchased from Gibco® Life Technology, Carslbad, USA. Cord blood-derived CD34+ progenitor cells were reprogrammed into iPSCs by using a three-plasmid and seven-factor episomal system (OCT4, Sox2, Myc, Klf4, Nanog, SV40LT and Lin28 antigen). iPSC lines were fully characterized by: a. immunostaining, b. qPCR, c. tri-lineage differentiation, d. teratoma essay, and e. karyotyping, as described in Example 2.

The iPSC line was cultured on Matrigel-coated 6-well culture plate with mTeSRTM1 medium (STEMCELL™ Technologies). Human iPSCs were maintained undifferentiated with a daily medium change as the protocol described in Example 2.

Cardiomyocyte Isolation and Immunofluorescent Characterization

Cardiomyocyte aggregates were dissociated by using Accutase™ (STEMCELL™ Technologies). Following a DPBS wash, Accutase™ was added to the cardiomyocytes for 8 minutes at 37° C. After the addition of 2-3 volume of fresh CMM to terminate the reaction of Accutase™, the cells were firstly physically detached and collected by 1000 uL pipette. Subsequently, dissociated cardiomyocytes were transferred and seeded to 1:30 Matrigel-coated polymer-made coverslip. They were cultured with CMM and 10 um Y-27683 for at least two days prior to immunofluorescent examination.

The dissociated iPSC-derived cardiomyocytes cultured on the polymer-made coverslips (ibidi Technologies) were washed with PBS and fixed with 4% paraformaldehyde (PFA) at room temperature for 20 minutes and then went through various steps of staining as described in Example 2 in details. The immunocytochemistry images were analyzed by ImageJ.

Single Cell RNA-Sequencing and Rt-qPCR

Human iPSC-derived cardiomyocytes were collected using the protocols described in Example 2 and were fixed by chilled methanol and stored on ice for 15 minutes for fixation prior to −80° C. storage. The fixed cells were rehydrated using a FACS Aria II or FACSJazz (BD Biosciences). Single cells (based on DAPI exclusion and forward/side scatter properties) were sorted into 384-well hard-shell plates (Biorad) with 5 μl of vapor-lock (QIAGEN) containing 100-200 nl of RT primers, dNTPs and synthetic mRNA Spike-Ins and immediately spun down and frozen to −80° C. Sort-sequencing was used for single cell RNAseq. In brief, cardiomyocytes were lysed by 5 min at 65° C., when RT and second strand mixes were dispersed with the Nanodrop II liquid handling platform (GC biotech). Aqueous phase was separated from the oil phase after pooling all cardiomyocytes in one library, followed by IVT transcription. For library preparation, the CEL-Seq2 protocol was applied. Primers were composed of a 4 bp random molecular barcode, 24 bp polyT stretch, a T7 promoter, a cell-specific 8 bp barcode, and the 5' Illumina TruSeq small RNA kit adaptor. Single-cell mRNA was subsequently reverse transcribed, converted to double-stranded cDNA, assembled and in vitro transcribed to linear as required for the CEL-Seq 2 protocol (Hashimshony et al., 2016). Illumina sequencing libraries were then made with the TruSeq small RNA primers (Illumina) and sequenced paired-end at 75 bp read length the Illumina NextSeq. Read alignment was performed. Subsequently, candidate cells and genes were analysed in R environment. Cells were filtered using a criterion wherein transcript number >12,000 and gene were filtered >5 transcript in more than 5 cells. t-sne plot and differentiation gene expression analysis were performed based on R package RaceID (v0.1.5). Violin plots were generated by using R package ggplot2 (v3.2.1) and heatmaps were made by using R package ComplexHeatmap(v2.1.2). Gene filtering was avoided to present all interested genes in the heatmap.

For RT-qPCR, various gene expressions were analysed to identify the derived cells as CMs, and to subsequently identify the subtype specificity of the derived CMs. Quantitative PCR analysis was conducted for early cardiac marker (Nkx2.5), cardiac troponin coding gene (Tnnt2), atrial specific genes (Nppa, Myl7 and Kcnj5), inward rectifier potassium channel coding genes (Kcnj2, Kcnj4, Kcnj5 and Kcnj12), Gremlin-2 protein coding gene (Gremlin2), and beta-1 adrenergic receptor coding gene (Adrb1) in experimental and control groups. All the TaqMan® Gene Expression Assays were predesigned by Applied Biosystems by Thermo Fisher Scientific. Quantitative PCR was performed with LightCycler®480 (Roche) using TaqMan® Gene Expression Master Mix (Applied Biosystems by Thermo Fisher Scientific) under the instructions from the manufacturer.

Electrophysiological Studies and $Ca^{2+}$ Imaging

Action potential recording was recorded by patch clamp under a whole-cell configuration using Axon 700B amplifier system (Molecular Devices, USA). The pipette solution contained (in mmol/L): K-aspartate (K-Asp) 136, KCl 5.4, NaCl 5, $MgCl_2$ 1, HEPES 1, EGTA 5, MgATP 5, Phosphocreatine 5, pH 7.2 with KOH. The bath solution consisted of (in mmol/L) NaCl 136, KCl 5.4, $MgCl_2$ 1.0, $CaCl_2$ 1.8, $NaH_2PO_4$ 0.33, HEPES 5, Glucose 10, pH 7.4 with NaOH.

Optical mapping experiments were carried out after the cells started to contract. The responsiveness of the derived CMs in the experimental group to β and α adrenergic receptor agonists and antagonists was measured. Intracellular calcium transients were analysed using a 128×128 EMCCD camera (Photometrics, Tucson, USA). The derived CMs were pre-loaded with 1 μM Fluo4 (Molecular Probes by Life Technologies) dissolved in DMSO for 15 min at 37° C. in CMM. Calcium transients of the derived CMs were first recorded without the addition of the drugs as control. Recordings were then taken at 0 min, 5 min, 10 min and 15 min after 100 nM Isoprenaline (ISO) treatment. Using the same method, the responsiveness of the derived CMs in the experimental group to 10 μM Phenylephrine (PE) treatment was tested. In adrenergic receptor antagonist tests, the cells were pre-treated with 600 nM CGP20712A (CGP) (Sigma) dissolved in Fluo4 loading solution prior to 100 nM ISO treatment. Recordings were taken in the same way as described above. Similarly, the cells were pre-treated with 1 μM Prazosin dissolved in Fluo4 loading solution before a treatment of 10 μM PE. Metamorph was used to take the recordings, and 4000 or 8000 frames were taken for each recording, with a frame rate of 100 Hz (for 4000 frames) or 333.33 Hz (for 8000 frames). Regions of interest were selected using ImageJ. Raw traces were analysed and baseline corrections were conducted using Clampfit. Calcium transient amplitude change was calculated based on averaged trace. Part of the analysis was performed using custom MATLAB algorithms. To calculate beat-to-beat CaT50, the mean signal was segmented into individual beats. Representative regions were defined as two 16 by 16 pixel regions.

Example 2: Additional Methods hiPSC Cell Line: Episomal Human iPSC Line

The iPSCs line used for the cardiomyocyte differentiation was purchased from Gibco® Life Technology, Carslbad, USA. Cord blood-derived CD34+ progenitor cells were reprogrammed into iPSCs by using a three-plasmid and seven-factor episomal system (OCT4, Sox2, Myc, Klf4, Nanog, SV40LT and Lin28 antigen).

iPSC Culturing and Differentiation

Cells of the iPSC line were cultured on Matrigel-coated 6-well culture plates with mTeSRTM1 medium (STEMCELL™ Technologies), human iPSCs were maintained undifferentiated with daily medium change. mTeSRTM1 medium was pre-warmed under room temperature every time before use. The iPSCs were passaged every 4 days (mTeSRTM1) when cells achieved an approximately 70% confluency. On differentiation day 0, human iPSCs were sufficiently dissociated into single cells for cardiomyocyte differentiation. iPSCs were washed by DPBS and treated by ReLeSR™ for 40 seconds. When ReLeSR™ was aspirated, 1 ml Accutase™ (STEMCELL™ Technologies) was added on the cells and incubated at 37° C. for 5 min. After the addition of 2-3 volume of fresh mTeSRTM1 medium to terminate the reaction of Accutase™, the cells were plated on 1:30 diluted Matrigel-coated 4- or 24-well plates with mTeSRTM1 medium and 10 uM Y-27683. The plate was then moved following a forward-backward and left-right pattern to evenly distribute iPSCs. These cells were fed daily with mTeSRTM1 medium and 10 uM Y-27683 to support single cell proliferation until they achieve 80% confluency. (Note: The even distribution of fully-separated single iPSCs is critical for successful CM differentiation).

Differentiation experiments were performed by using PSC Cardiac Differentiation Kit (Gibco® Life Technology) consisting of Cardiac Differentiation Medium A(CDMA), Cardiac Differentiation Medium B (CDMB) and Cardiac Maintenance Medium (CMM). When the iPSCs reached 80% confluency, CDMA with 10 uM Y-27683 was added to the plates and the date of adding CDMA was labelled as Differentiation day 0 (Day 0). CDMB with 10 uM Y-27683 was fed on Day 2. From Day 4, the cells were cultured with CMM and the medium was changed every other day. All the differentiation and culture media were pre-warmed under room temperature before use. The differentiating cells were distinguished into experimental group and control group. For experimental group, Gremlin 2 (R&D system) was applied to the cells at the final concentration of 1 ug/ml on Day 4, and retinoic acid (Sigma-Aldrich Corporation) was applied to the cells at the final concentration of 1 uM on Day 6 and Day 8. The control group was differentiated by the same protocol without the involvement of Gremlin 2 and retinoic acid.

Cardiomyocyte Dissociation

Cardiomyocyte aggregates were dissociated by using Accutase™ (STEMCELL™ Technologies). Following a DPBS wash, Accutase™ was added to the cardiomyocytes for 8 minutes at 37° C. After the addition of 2-3 volume of fresh CMM to terminate the reaction of Accutase™, the cells were firstly physically detached and collected by 1000 uL pipette. Subsequently, dissociated cardiomyocytes were transferred and seeded to 1:30 Matrigel-coated polymer-made coverslip. They were cultured with CMM and 10 um Y-27683 for at least two days prior to immunofluorescent examination.

Figure 1B:
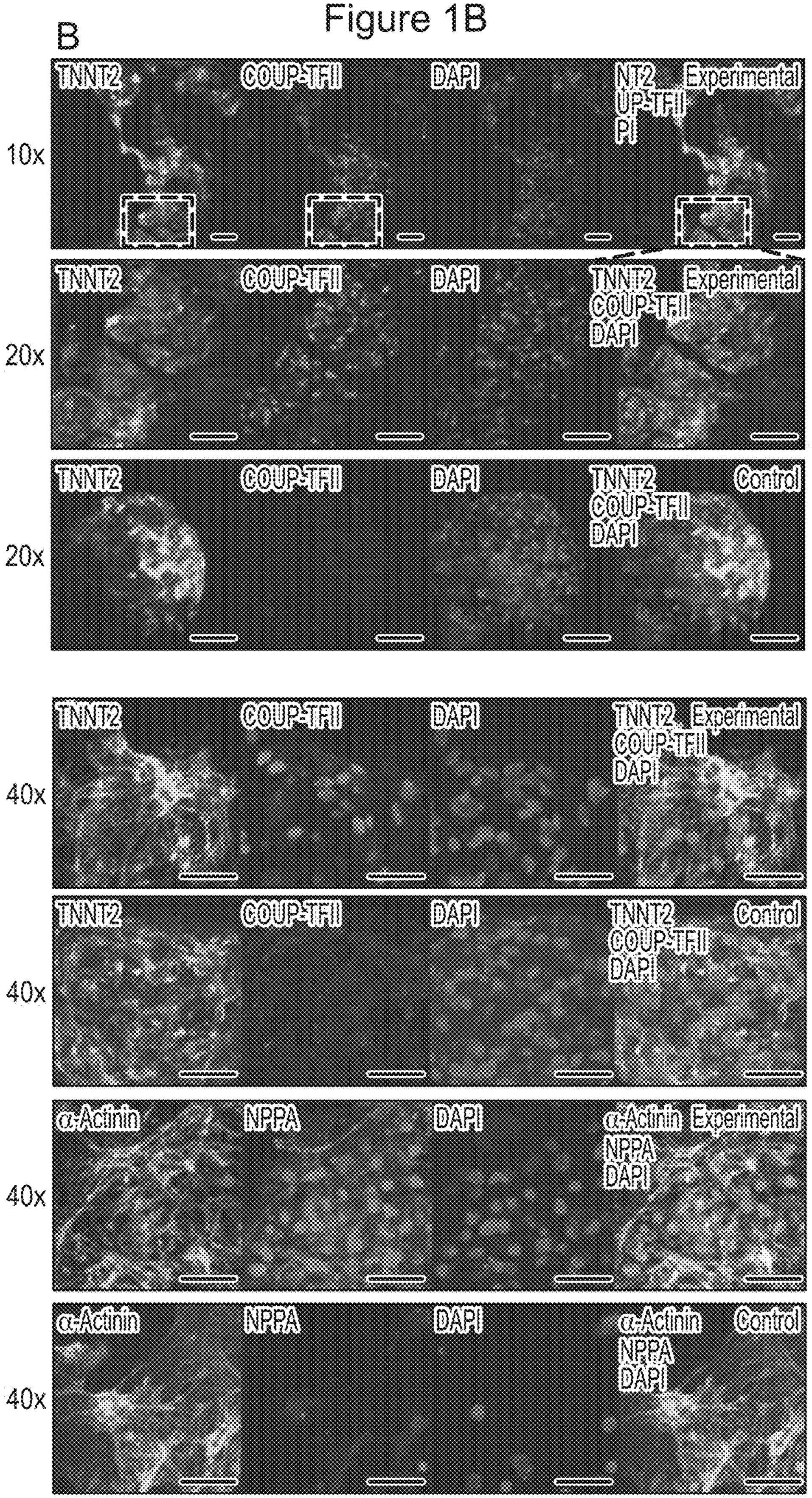

Immunofluorescence Analysis (for FIG. 1B)

The dissociated iPSC-derived cardiomyocytes cultured on the conventional glass coverslip or polymer-made coverslips (ibidi Technologies) were washed with PBS and fixed with 4% paraformaldehyde (PFA) at room temperature for 20 minutes. After fixation, the cells were washed 3 times with ice-cold PBS, and permeabilized by 0.1% Triton X-100 in PBS for 20 minutes and wash by PBS three times. Then, they were blocked from non-specific binding by 10% goat serum diluted in 0.1% Tween-20 in PBS (PBST) for 60 min at room temperature. Subsequently, the cardiomyocytes were incubated with primary antibodies diluted in 1% goat serum in PBST in a humidified chamber overnight at 4° C. The dilution for each antibody is listed in Table 2. After the primary antibody incubation, cardiomyocytes were washed with PBS three times and incubated with secondary antibody diluted in 1% goat serum in PBST for 1.5 hour at room temperature. After the secondary antibody incubation, the cells were washed for three times with PBS at room temperature. All operations after the involvement of secondary antibody were performed in a dark room. Then another glass-made coverslip was transferred onto the ibidi coverslip and mounted with Prolong™ Gold Antifade Reagent Mounting medium with DAPI (Molecular Probes by Life Technologies). Followed by snail polish sealing, the slides can be examined directly or stored in 4° C. for approximate one month. The immunocytochemistry images were analyzed by ImageJ.

Single Cell RNA-Sequencing

1. Single-Cell Dissociation and Methanol Fixation

Human iPSC-derived cardiomyocytes were briefly washed by DPBS and treated by 300 uL pre-warmed 100 U/mL Collagenase I (Gibco® Life Technology) dissolved in RPMI 1640 medium (Gibco® Life Technology) for 40 minutes at 37° C. Then the cells were detached by using 1000 uL pipette and return to 37° C. for another 10 minutes. Digested cardiomyocytes were then transferred into 1.5 mL centrifuge tube containing 1 mL CMM to dampen the reaction. After the centrifugation at 300rcf for 3 min using Centrifuge 5424R (Eppendorf), the supernatant was discarded when the cardiomyocyte pellet was resuspended in 0.3 mL Accutase (STEM CELL Technologies) and incubated at 37° C. for 10 min. Afterward, 1 mL chilled DPBS was applied to the cells to stop the reaction and was subsequently filtered through a 70 mm cell strainer to acquire single cells. The filtered cells were then centrifuged at 300 rcf for 3 mins at 4° C. to reduce cell debris. When supernatant was discarded, the pellet was resuspended by 100 uL chilled DPBS, followed by 900 uL chilled methanol and stored on ice for 15 minutes for fixation prior to −80° C. storage.

2. Single-Cell Sorting into 384-Well Hard-Shell Plate (This protocol was provided by Single Cell Discoveries B.V.). The fixed cells were rehydrated by applying centrifugation at 3000 rcf for 10 min at 4° C., followed by supernatant removal and chilled Rehydration Buffer resuspension (1 mL). After using a wide-bored pipette tip to gently pipette mix the cell solution 10 times, the cells were centrifuged, and resuspended following an identical process to that described above to achieve a target cell concentration of $7\times10^5$-$1.2\times10^6$/ml). The rehydrated cells were immediately sorted using a FACS Aria II or FACSJazz (BD biosciences). Single cells (based on DAPI exclusion and forward/side scatter properties) were sorted into 384-well hard-shell plates (Biorad) with 5 μl of vapor-lock (QIAGEN) containing 100-200 nl of RT primers, dNTPs and synthetic mRNA Spike-Ins and immediately spun down and frozen to −80° C.

3. Sort-Sequencing (This protocol was provided by Single Cell Discoveries B.V.). For SORT-seq, cardiomyocytes were lysed by 5 min at 65° C., when RT and second strand mixes were dispersed with the Nanodrop II liquid handling platform (GC biotech). Aqueous phase was separated from the oil phase after pooling all cardiomyocytes in one library, followed by IVT transcription. For library preparation, CEL-Seq2 protocol was applied. Primers was composed of a 4 bp random molecular barcode, 24 bp polyT stretch, a T7 promoter, a cell-specific 8 bp barcode, and the 5'-Illumina TruSeq small RNA kit adaptor. Single-cell mRNA was subsequently reverse transcribed, converted to double-stranded cDNA, assembled and in vitro transcribed for linear as required for the CEL-Seq 2 protocol (Hashimshony et al., 2016). Illumina sequencing libraries were then made with the TruSeq small RNA primers (Illumina) and sequenced paired-end at 75 bp read length the Illumina NextSeq.

4. scRNAseg Analysis

Read alignment was performed. Subsequently, candidate cells and genes were analyzed in R environment. Cells were filtered using a criterion wherein transcript number >12,000 and gene were filtered >5 transcript in more than 5 cells. t-sne plot and differentiation gene expression analyses were performed based on R package RaceID (v0.1.5). Violin plots were generated by using R package ggplot2 (v3.2.1) and heatmaps were made by using R package ComplexHeatmap (v2.1.2). Gene filtering was avoided to present all interested gene in heatmap.

TABLE 1

Summary of applied antibodies

| Primary Antibody | | | | |
|---|---|---|---|---|
| Target | Host | Dilution | Code | Supplier |
| α-Actinin | Mouse | 1:10000 | A7811 | Sigma-Aldrich Corporation |
| α-Actinin | Mouse | 1:200 | Ab9465 | Abcam |
| TNNT2 | Mouse | 1:800 | WI 53719 | MOLECULAR PROBES |
| COUP-TFII | Rabbit | 1:100 | Ab211777 | Abcam |
| NPPA | Rabbit | 1:100 | Ab209232 | Abcam |
| TRA-1-60 | Mouse | 1:100 | MAB4360 | EMD Millipore Corporation |
| OCT-4 | Rabbit | 1:500 | ABD116 | EMD Millipore Corporation |

| Secondary Antibody | | | | | |
|---|---|---|---|---|---|
| Target | Host | Dilution | Code | Fluorescence | Supplier |
| Mouse | Goat | 1:400 | AP128C | Cy3 | CHEMICON International |
| Mouse | Goat | 1:1000 | Ab150117 | Alexa Fluo 488 | Abcam |
| Rabbit | Goat | 1:250 | AP132S | Cy5 | CHEMICON International |

RT-qPCR

Various gene expressions were analysed to identify the derived cells as CMs, and to subsequently identify the subtype specificity of the derived CMs. Quantitative PCR analysis was conducted for early cardiac marker (Nkx2.5), cardiac troponin coding gene (Tnnt2), atrial specific genes (Nppa, Myl7 and Kcnj5), inward rectifier potassium channel coding genes (Kcnj2, Kcnj4, Kcnj5 and Kcnj12), Gremlin-2 protein coding gene (Gremlin2), and beta-1 adrenergic receptor coding gene (Adrb1) in experimental and control groups. All the TaqMan® Gene Expression Assays were predesigned by Applied Biosystems by Thermo Fisher Scientific. Quantitative PCR was performed with LightCycler®480 (Roche) using TaqMan® Gene Expression Master Mix (Applied Biosystems by Thermo Fisher Scientific) under the instructions from the manufacturer. In brief, for a total reaction volume of 20 μl, 10 μl of Gene Expression Master Mix, 1 μl of Gene Expression Assays, 1 μl of cDNA sample and 8 μl of RNase-free water were used. Cycling parameters were 2 min at 50° C., followed by 10 minutes at 95° C., then followed by 40 cycles of 15 seconds at 95° C. and 60 seconds at 60° C. A control for cDNA input was generated by amplifying HPRT1 gene (Applied Biosystems by Life Technologies). The relative gene expression was determined by averaging the results of two or three technical replicates, and comparing the Ct values of genes of interest with those of the control gene using ΔΔCt method.

| Gene | Assay no. | Target species |
|---|---|---|
| Tnnt2 | Hs00943911_m1 | Human |
| Nkx2.5 | Hs00231763_m1 | Human |
| Grem2 | Hs03986140_s1 | Human |
| Nppa | Hs00383231_m1 | Human |
| Myl7 | Hs01085598_g1 | Human |
| Kcna5 | Hs00969279_s1 | Human |
| Kcnj5 | Hs00168476_m1 | Human |
| Kcnj2 | Hs01876357_s1 | Human |
| Kcnj4 | Hs00705379_s1 | Human |
| Kcnj12 | Hs00266926_s1 | Human |
| Kcnj14 | Hs00601649_m1 | Human |
| Adra1a | Hs00169124_m1 | Human |
| Adrb1 | Hs02330048_s1 | Human |

Optical Mapping

Optical mapping experiments were carried out after the cells started to contract. The responsiveness of the derived CMs in the experimental group to β and a adrenergic receptor agonists and antagonists was measured. Intracellular calcium transients were analysed using a 128×128 EMCCD camera (Photometrics, Tucson, USA). The derived CMs were pre-loaded with 1 μM Fluo4 (Molecular Probes by Life Technologies) dissolved in DMSO for 15 min at 37° C. in CMM. Calcium transients of the derived CMs were first recorded without the addition of the drugs as control. Recordings were then taken at 0 min, 5 min, 10 min and 15 min after 100 nM Isoprenaline (ISO) treatment. Using the same method, the responsiveness of the derived CMs in the experimental group to 10 μM Phenylephrine (PE) treatment was tested. In adrenergic receptor antagonist tests, the cells were pre-treated with 600 nM CGP20712A (CGP) (Sigma) dissolved in Fluo4 loading solution prior to 100 nM ISO treatment. Recordings were taken in the same way as described above. Similarly, the cells were pre-treated with 1 μM Prazosin dissolved in Fluo4 loading solution before a treatment of 10 μM PE. Metamorph was used to take the recordings, and 4000 or 8000 frames were taken for each recording, with a frame rate of 100 Hz (for 4000 frames) or 333.33 Hz (for 8000 frames). Regions of interest were selected using ImageJ. Raw traces were analyzed and baseline corrections were conducted using Clampfit. Calcium transient amplitude change was calculated based on averaged trace. Part of the analysis was performed by the collaborator group from University of Birmingham using custom MATLAB algorithms. To calculate beat-to-beat CaT50, the mean signal was segmented into individual beats. Representative regions were defined as two 16 by 16 pixel regions.

Electrophysiological Studies

Action potential recordings of the experimental group cells were obtained by patch clamp under whole-cell configuration using Axon 700B amplifier system (Molecular Devices, USA) in the pipette solution consisting of 136 mmol/L K-aspartate (K-Asp), 5.4 mmol/L KCl, 5 mmol/L NaCl, 1 mmol/L $MgCl_2$, 1 mmol/L HEPES, 5 mmol/L EGTA, MgATP 5 mmol/L and 5 mmol/L Phosphocreatine. The pH value was adjusted to 7.2 with KOH. The bath solution was composed of 136 mmol/L NaCl, 5.4 mmol/L KCl, 1.0 mmol/L $MgCl_2$, 1.8 mmol/L $CaCl_2$, 0.33 mmol/L $NaH_2PO_4$, 5 mmol/L HEPES and 10 mmol/L Glucose. The pH value was adjusted to 7.4 with NaOH.

Statistical Analysis

Statistical analysis was done using Microsoft® Excel version 15.38 for mac and GraphPad Prism® Version 6.0c for Mac. All the data were presented as Mean±SEM. A parametric T test was performed to test for significance. (*) indicates P value<0.05, () indicates P value<0.01, (*) indicates P value<0.001 and (****) indicates P value<0.0001.

Electrophysiological Recording

Action potential recording was recorded by patch clamp under a whole-cell configuration using Axon 700B amplifier system (Molecular Devices, USA). The pipette solution contained (in mmol/L): K-aspartate (K-Asp) 136, KCl 5.4, NaCl 5, $MgCl_2$ 1, HEPES 1, EGTA 5, MgATP 5, Phosphocreatine 5, pH 7.2 with KOH. The bath solution consisted of (in mmol/L) NaCl 136, KCl 5.4, $MgCl_2$ 1.0, $CaCl_2$ 1.8, $NaH_2PO_4$ 0.33, HEPES 5, Glucose 10, pH 7.4 with NaOH.

Confocal Microscopy

IPS-CM cultured in cover slip were fixed with 4% paraformaldehyde for 15 min and were then blocked with 5% BSA for 1 h. 0.1% Triton-X100 was used for membrane permeabilization. Then, cells were incubated with the primary mouse anti-actinin 2 antibody (Boster, Wuhan, China) at 4° C. overnight. After washing with cold PBS, cells were incubated for 1 h at room temperature with DyLight® 488-conjugated donkey anti-mouse secondary antibody (1:200, Abcam, Cambridge, UK). Cells were incubated with Rhodamine phalloidin (Cytoskeleton, USA) for 30 min, an F-actin probe conjugated to red-orange fluorescent dye. DAPI was used for staining the nucleus for 5 min. Immunofluorescence-labelled samples were examined using a Nikon confocal laser scanning microscope (Tokyo, Japan).

Example 3: Morphological and Immuno-Cytochemical Characterization

FIG. 1A shows a schematic of the atrial-specific differentiation protocol. In this protocol, Gremlin 2 was added prior to RA based on its unique function to first inhibit BMP signalling and then to subsequently promote this signalling at a later stage. Properties of the derived cardiomyocytes including cell subtype, maturation status and physiological functionality were investigated in the tests described below.

The cells prepared from control and Grem2/RA treatment (defined as the experimental group) groups were characterized by immunocytochemistry to determine their morphology and expression of particular proteins that are specific for cardiac myocytes, including those expressed specifically in atrial myocytes. FIG. 1A shows labelling of the cytoskeletal protein α-actinin and TNNT2 (coding for cardiac troponin A) in both untreated and experimental (day 20) cell cultures, while labelling for atrial specific NPPA (coding for natriuretic peptide A) and COUP-TFII (also known as nuclear family receptor 2, Group F, member 2) was clearly evident in the experimental but not untreated cell cultures.

Further immunohistochemistry was carried out in individual cells following dispersal of cell cultures (see Examples 1 and 2). Again, the cytoskeleton marker α-actinin and TNNT were labelled in both untreated and experimental groups, but the experimental group cells showed clear expression of the atrial-specific markers COUP-TFII and NPPA, in contrast to the cells from untreated control cultures.

Figure 1C:
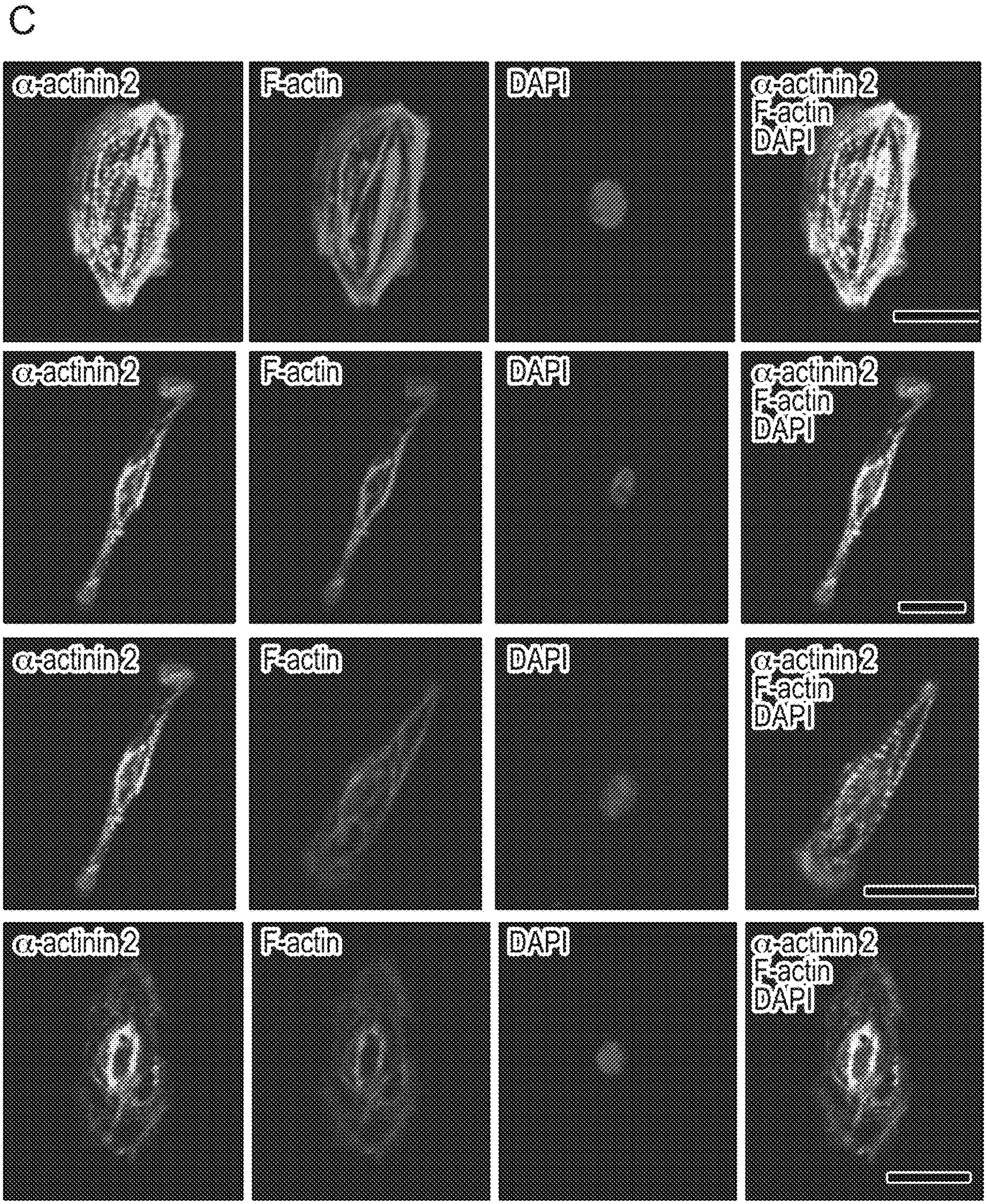

It is striking in FIG. 1C that the morphology of some of iPSC-AMs was remarkably similar to that of adult atrial CMs observed in human and animal hearts (Smyrnias, Mair, Harzheim, Walker, Roderick & Bootman, 2010; Zhang et al., 2013)). A rod and elongated shape morphology resembling the adult phenotype is particularly clear in the examples in the middle two panels of FIG. 1C, which is comparable to that reported in human mature CMs.

Figure 1D:
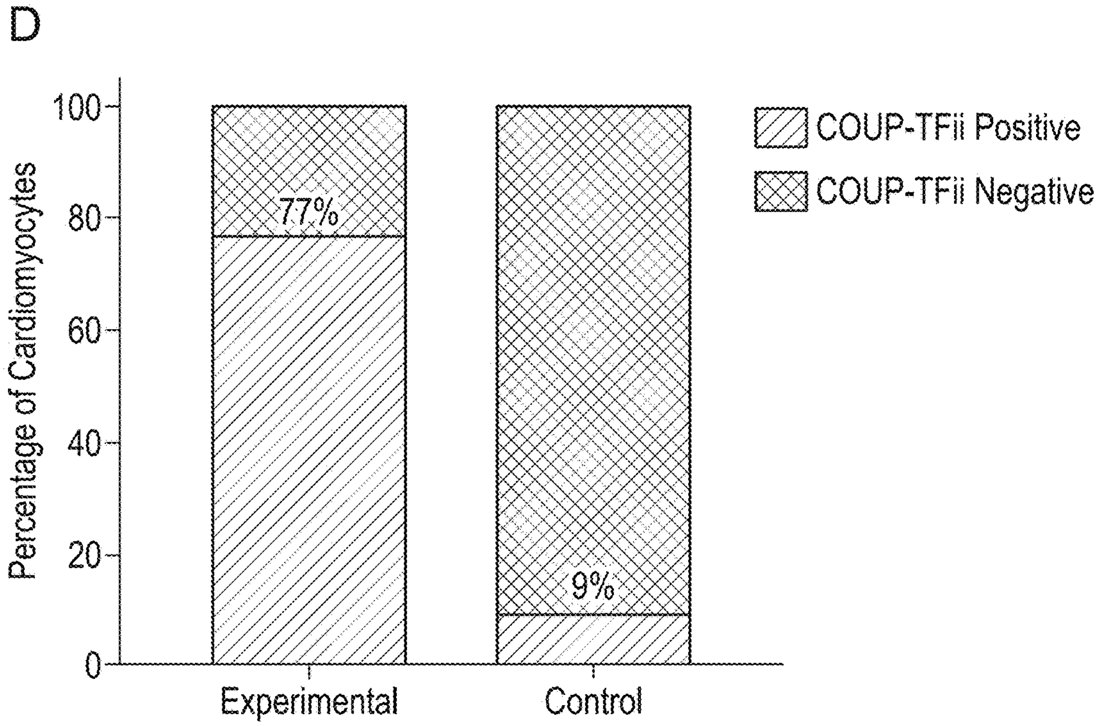

Furthermore, the cells differentiated by Gremlin2/RA protocol treatment also showed well organized sarcomere pattern with striation (sarcomere spacing slightly less than 2 μm, FIG. 1C), a feature which is broadly observed in adult CM models (Smyrnias, Mair, Harzheim, Walker, Roderick & Bootman, 2010; Zhang et al., 2013). The percentage of myocytes in the experimental group that were positive for the atrial-specific COUP-TFII/NPPA reached approximately 80% from −100 counted cells, in contrast to less than 10% in the untreated group (FIG. 1D).

Example 4: Transcriptional Characterization

To gain insights into the molecular signature of the iPSC-AMs and their difference from the control iPSC-CMs, we performed transcriptome analysis by single cell RNA sequencing on over 300 cells from each group. Unsupervised weighted gene co-expression network analysis revealed their transcription profiles.

Figure 2A:
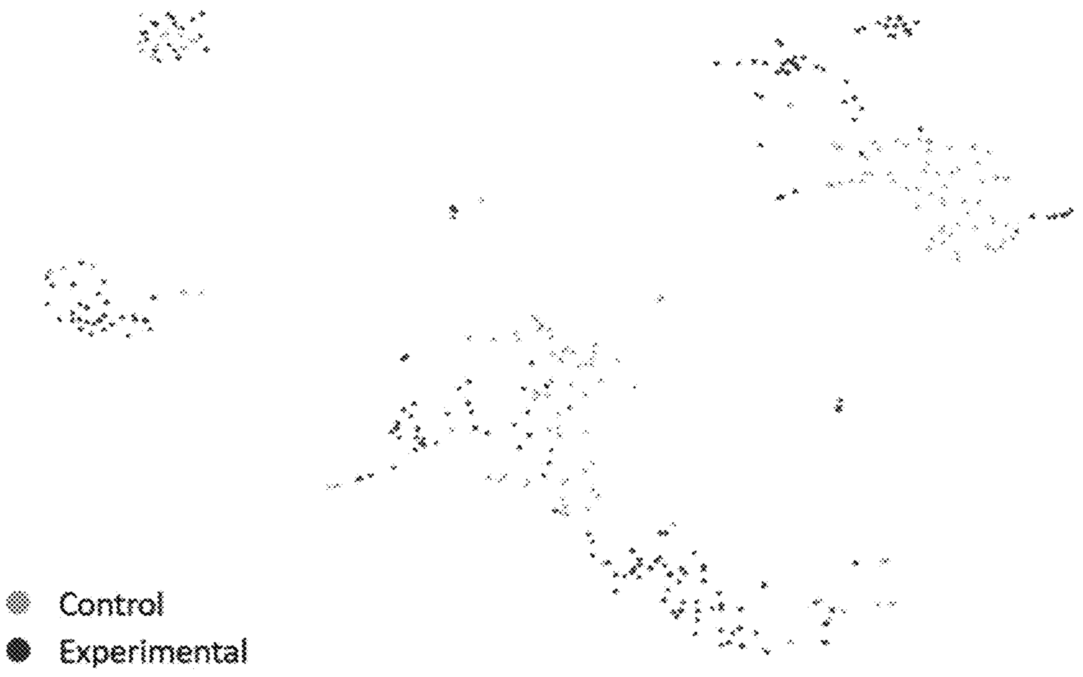
Figure 2B:
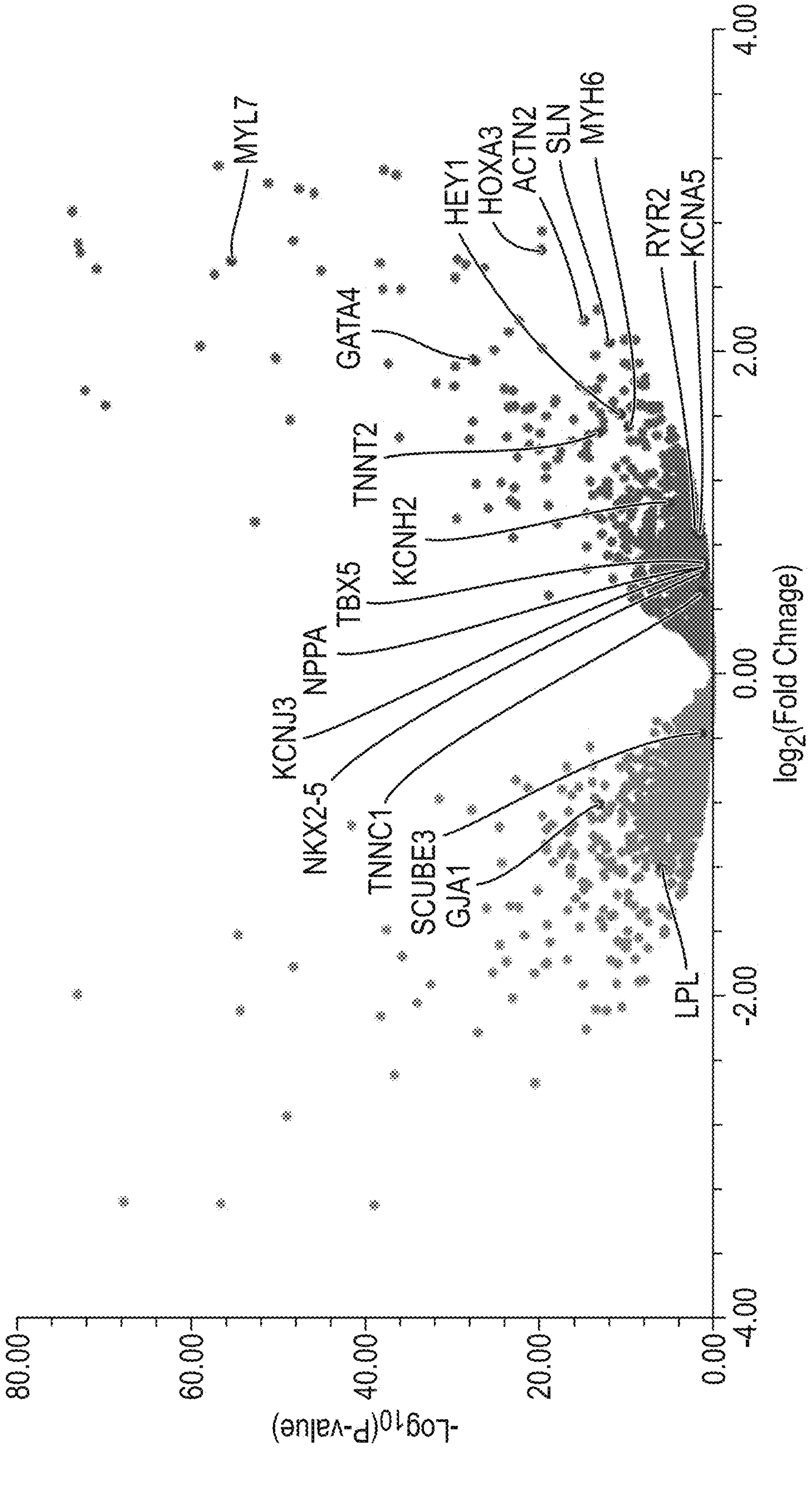

The t-SNE map (FIG. 2A) generated from quality-controlled single-cell transcriptomic profile showed clear differences between iPSC-derived cardiomyocytes from the experimental treated group and iPSC-derived cardiomyocytes from the control group. We subsequently identified the differential expression of genes between the experimental and untreated groups. Genes specific for atrial cardiomyocyte (i.e. MYL7, HEY1, HOXA1, SLN, MYH6, KCNH2, GATA4 and NPPA, etc.) were upregulated in the experimental group, while iPSC-CMs from the untreated group showed higher expression of certain ventricular cardiomyocyte-specific genes (i.e. GJA1, LPL and SCUBE3, etc.) (FIG. 2B). Notably, we found that genes encoding potassium channels Kv1.5 (KCNA5), and Kv11.1 (KCNH2) displayed significantly higher expression in iPSC-CMs from the experimental group compared with iPSC-CMs from the untreated group. These channels contribute to the shape and function APs in human atrial myocytes. KCNA5 encodes a subunit of a delayed rectifier potassium channel Kv1.5, underlying the ultra-rapidly activating delayed rectifier K+ current IKur found in human atrial (Feng, Wible, Li, Wang & Nattel, 1997).

Figure 2C:
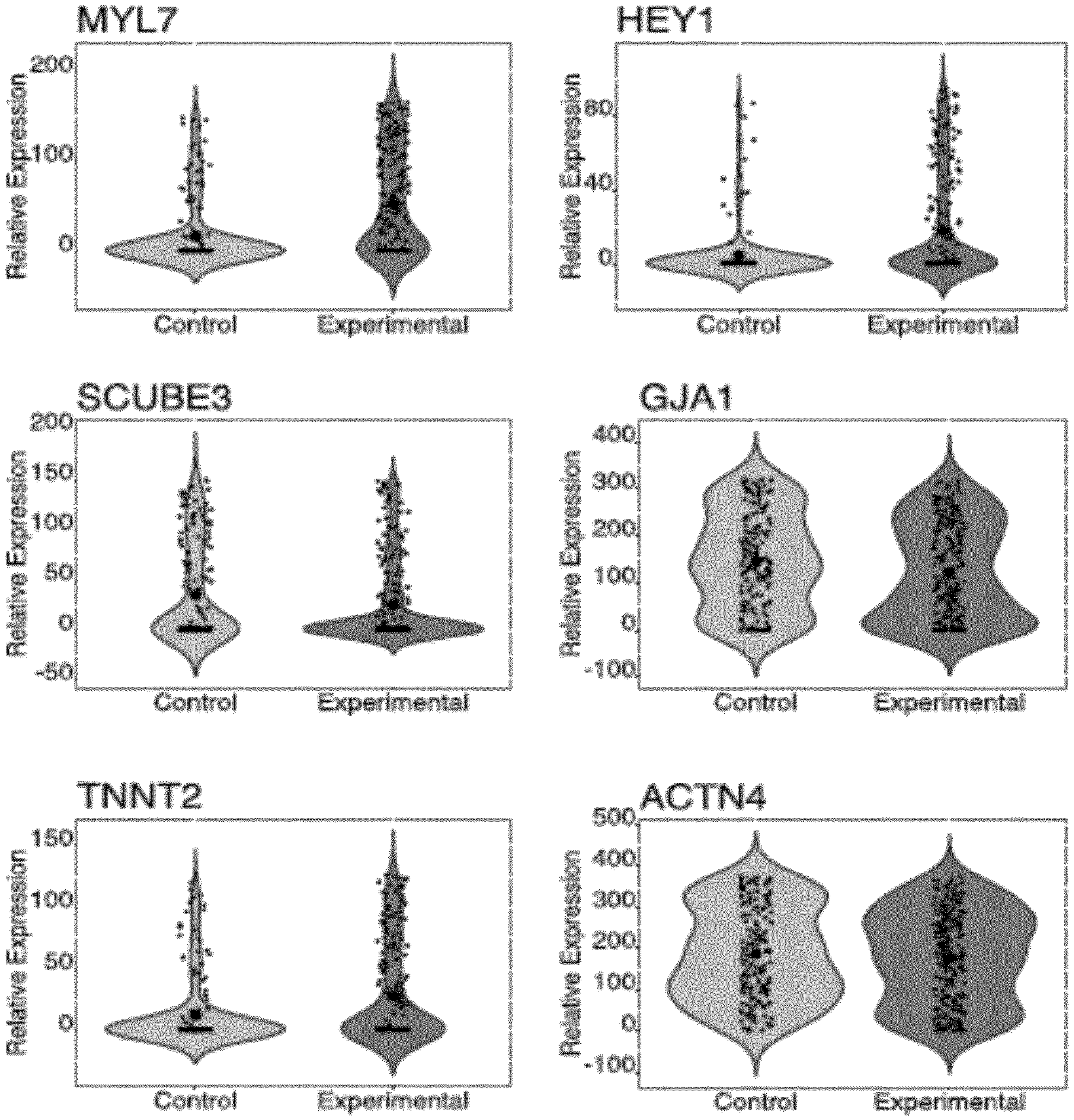
Figure 2D:
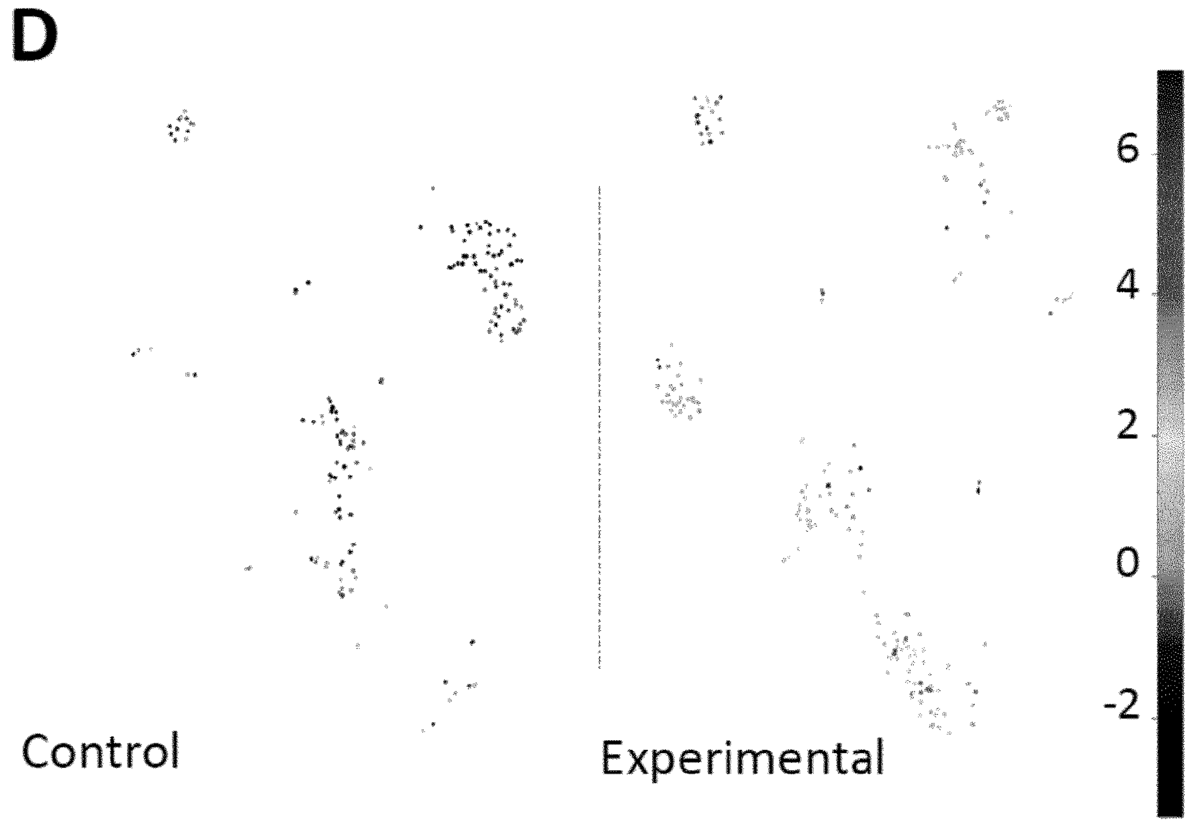
Figure 2E:
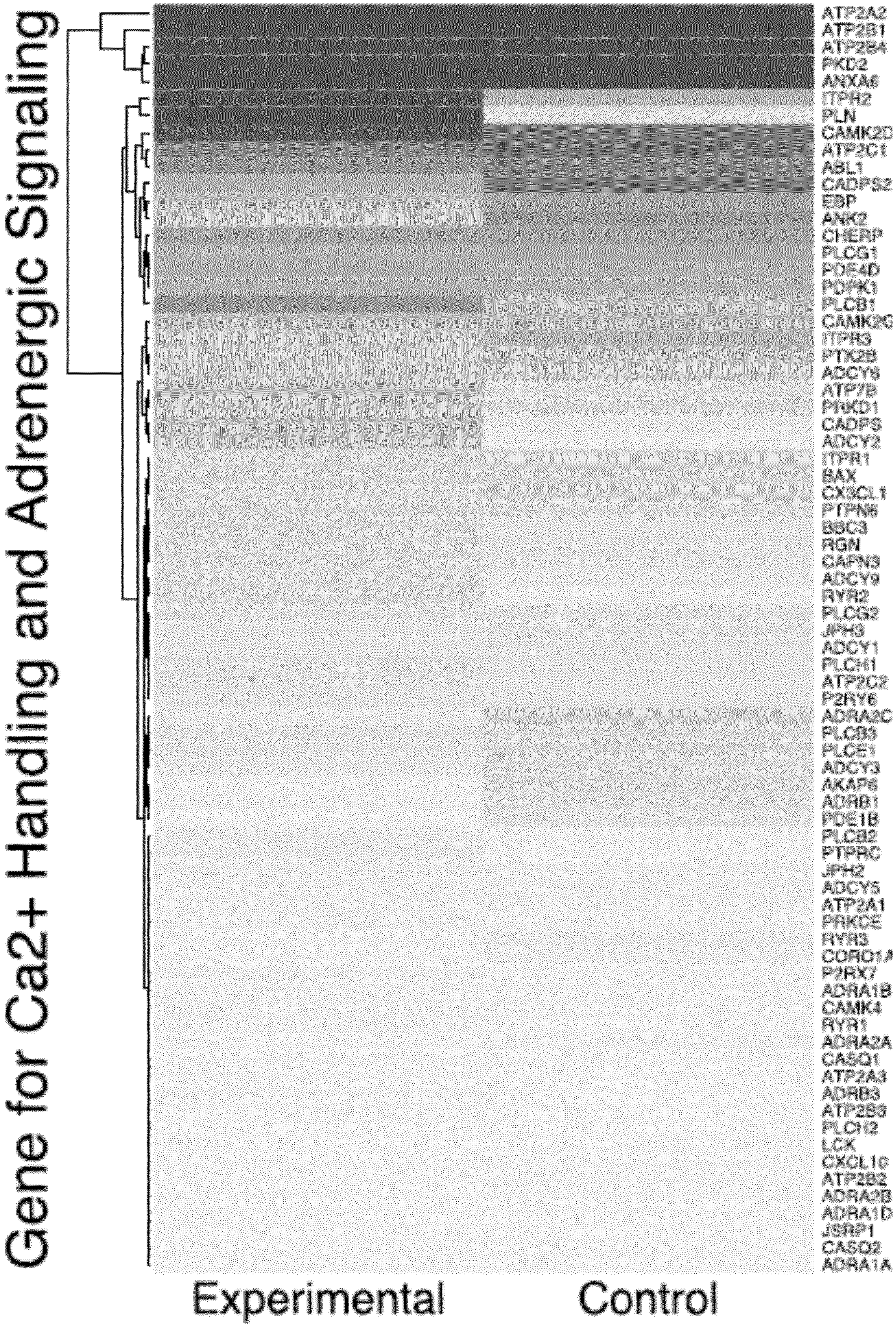

Expression of selected general, atrial and ventricular-specific genes in individual cardiomyocytes is shown in FIG. 2C. There was a higher proportion of iPSC-CMs from the experimental group expressing atrial genes MYL7 and HEY1 and a lower proportion of these cells expressing the ventricular gene SCUBE3, compared to counterpart cells from the untreated group. General cardiac genes like TNNT2 and ACTN4 were determined to show no significant differences between two groups, establishing a cardiac phenotype and comparable percentage of CMs in the samples.

Next, we counted the proportion of atrial cardiomyocytes in the experimental and untreated groups by averaging the expression of four critical atrial markers (HEY1, MYL7, HOXA3 and SLN). The experimental group showed a high expression of the four markers that are found in atrial cardiomyocytes. Using this method, it was established that an appropriate Gremlin2/RA treatment considerably increased the percentage of atrial cardiomyocytes from 16% in the untreated group to 71% in the experimental group. The averaged expression of HEY1, MYL7, HOXA3 and SLN in individual CM was highlighted in two separate t-SNE plots, representing either experimental or untreated groups (FIG. 2B).

We then determined the profiles of expression of calcium-handling and adrenergic-signalling genes (FIG. 2E), and ion channel genes (FIG. 2F) in experimental and untreated groups. Calcium handling genes like ATP2A2, ATP2B1, and ATP2B4 were highly expressed in cells of both groups. These genes encode intracellular pumps placed in the sarcoplasmic or endoplasmic reticula of CMs and catalyse the hydrolysis of ATP accompanying the translocation of $Ca^{2+}$ from the cytosol into the sarcoplasmic reticulum lumen, and these proteins are associated with the regulation of the muscular contraction/relaxation cycle (Olson, Wang, Carafoli, Strehler & McBride, 1991; Sakuntabhai et al., 1999). It is notable that iPSC-CMs from the experimental group demonstrated higher expression of ITPR2, encoding a member of inositol 1,4,5-triphosphate receptor family, and PLN, encoding an inhibitor of cardiac muscle sarcoplasmic reticulum $Ca(^{2+})$-ATPase (Rodriguez & Kranias, 2005; Yamamoto-Hino et al., 1994). In addition, both experimental and untreated groups strongly expressed certain ion channel genes, like ACTC1, CALM1, CALM3, UCHL1, GJA1, ATP1A1, COL6A1 and CLCN3, which is indicative of the functional electrophysiological properties of these cells.

Figure 2F:
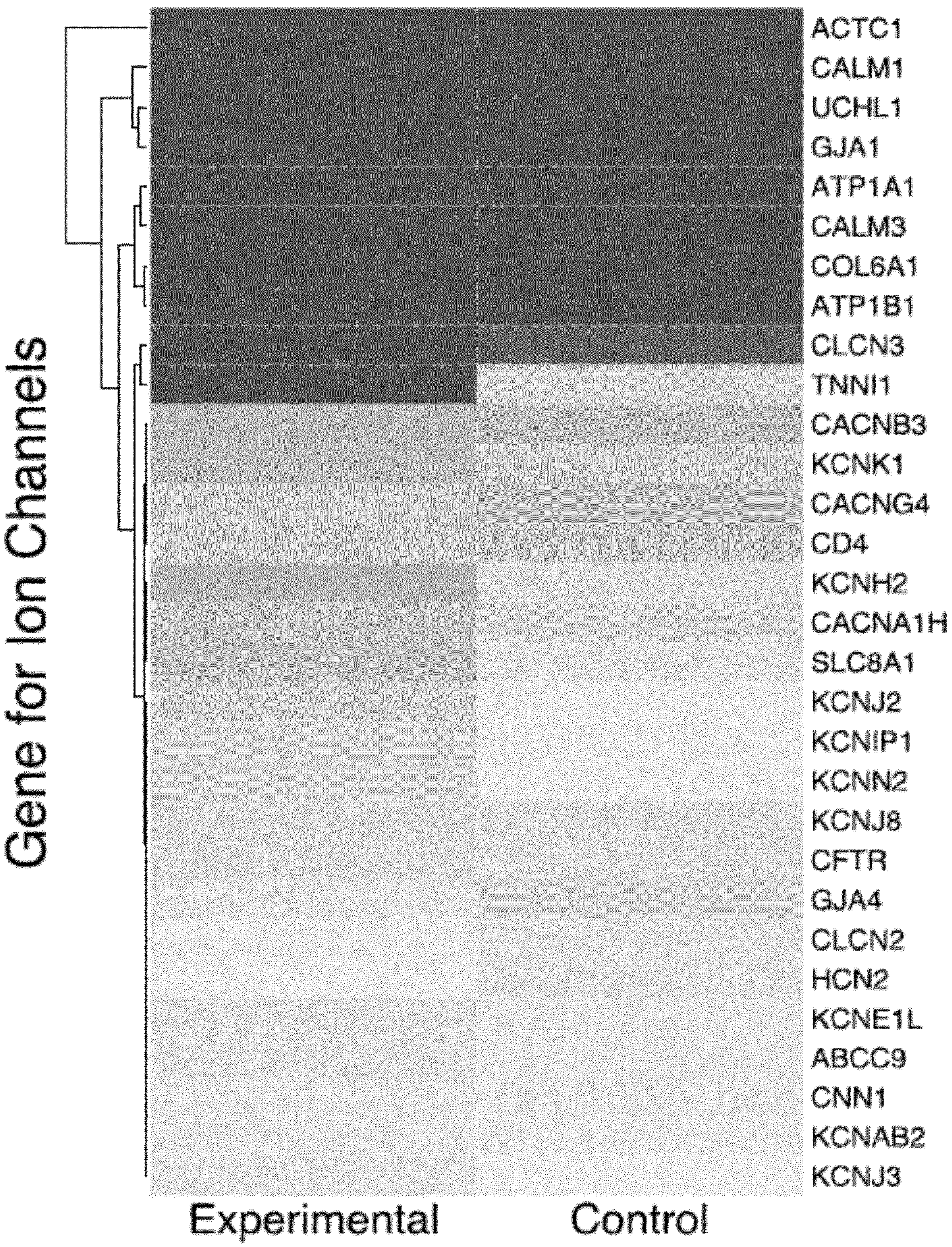
Figure 2G:
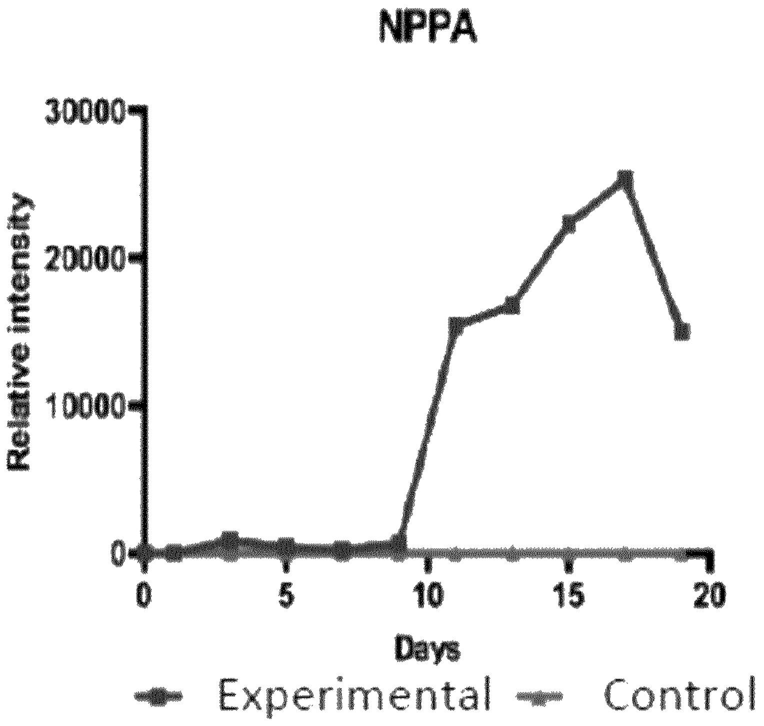
Figure 2G:
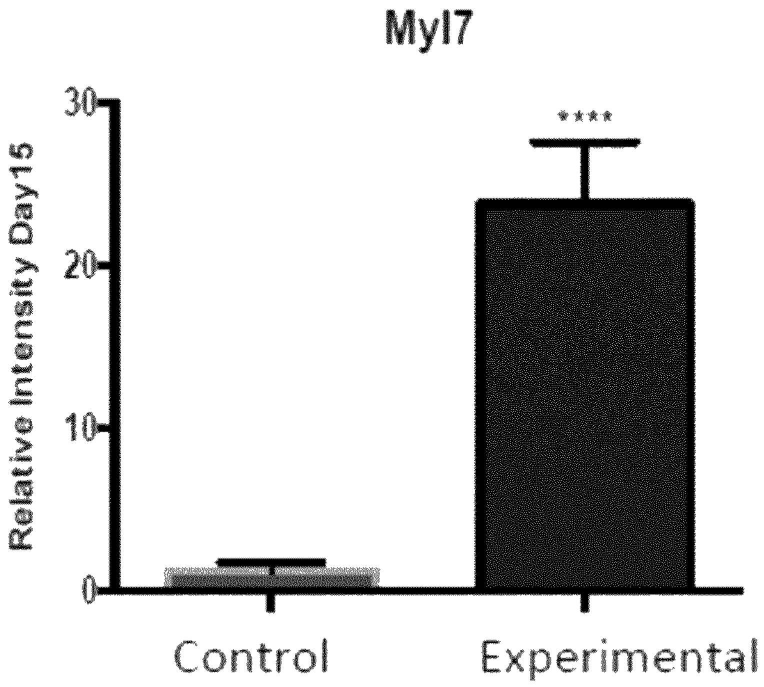

Furthermore, we performed a comparison of our human iPSC-CMs genetic dataset with a single-cell transcriptomic profile of adult mouse cardiomyocytes (FIG. 2F). The isolated adult mouse cardiomyocytes were prepared, sequenced and analyzed by an identical method. Heatmaps of the top 30 genes associated with ion channels were made by comparing observations from human iPSC-CMs and adult mouse cardiomyocytes. Both groups robustly expressed ACTC1, CALM1, ATP1A1, ATP1B1 and GJA1; human iPSC-CMs demonstrated an upregulated UCHL1, COL6A1 and CLCN3; the expression of TNNI3, SLC8A1, CACNA1C and KCNIP2 were apparently increased in adult mouse cardiomyocyte. Interestingly, TNNI1 is only upregulated in Gremlin2/RA-treated iPSC-CMs but not in untreated iPSC-CMs. Interestingly, Gremlin2/RA-treated hiPSC-CMs adult mouse CMs, have comparable gene expression contributing to electrophysiologic characteristics, suggesting that these cells had acquired certain level of electrical handling properties and reached a reasonable maturity.

Quantitative PCR analysis was further conducted for validating the scRNASeq results. As shown in FIG. 2, comparing the experimental cells to the untreated group, there was a significant high level of expression of atrial specific genes NPPA, My17 and genes that were preferentially expressed in atrial myocytes (KCNJ2, KCNJ5, KCNJ12, KCNA5) in cells from the Grem2/RA treatment group. For example, the expression of Myl7, the gene encoding myosin light chain 2 atrial isoform (MLC2a), is 20 fold higher in cells from Grem2/RA treatment group than in iPSC-CMs differentiated by a different conventional protocol, which is consistent with abundance of Myl7 in adult atrial cardiomyocytes. Expression of the KCNJ2 gene that encodes Kir2.1 for the cardiac inward rectifier potassium current (IK1) and is known for stabilizing the resting membrane potential was significant higher in cells of Grem2/RA treated experimental group than was observed in cells from the untreated group.

Example 5: Electrophysiological Characterizations

It is well known that the electrophysiological properties of atrial CMs are distinct from those of ventricular CMs. The resting membrane potential for human atrial myocytes has been found to be approximately −74 mV, which is relative more depolarized than is the case in ventricular cells (having a resting membrane potential of about −81 mV), while action potentials in atrial cells have a smaller upstroke amplitude and show an absence of a prominent plateau phase during the repolarization process (Grandi et al., 2011). Observations in animal models also showed that atrial cells have smaller amplitude and shorter duration action potentials (Giles & Imaizumi, 1988).

Figure 3A:
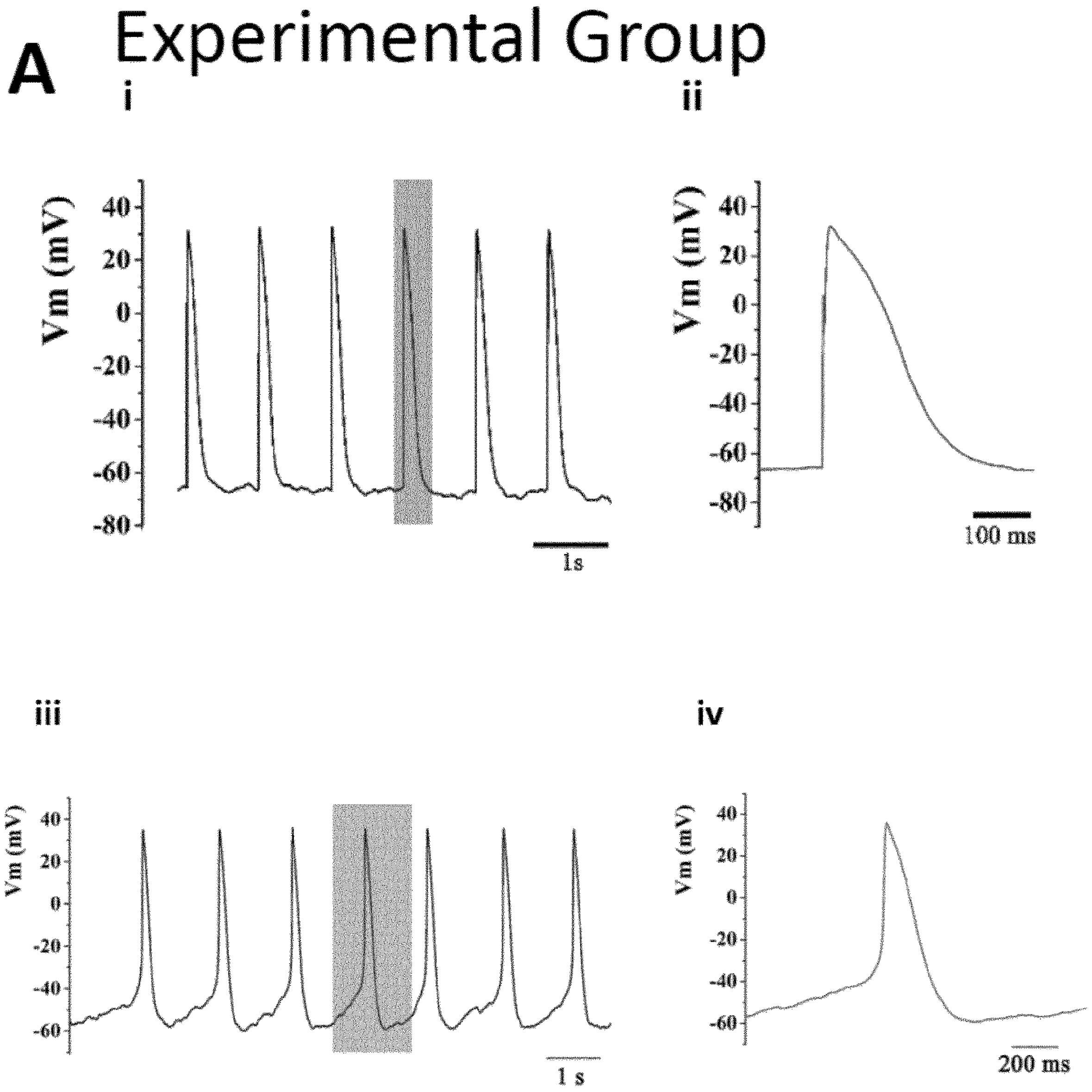
Figure 3B:
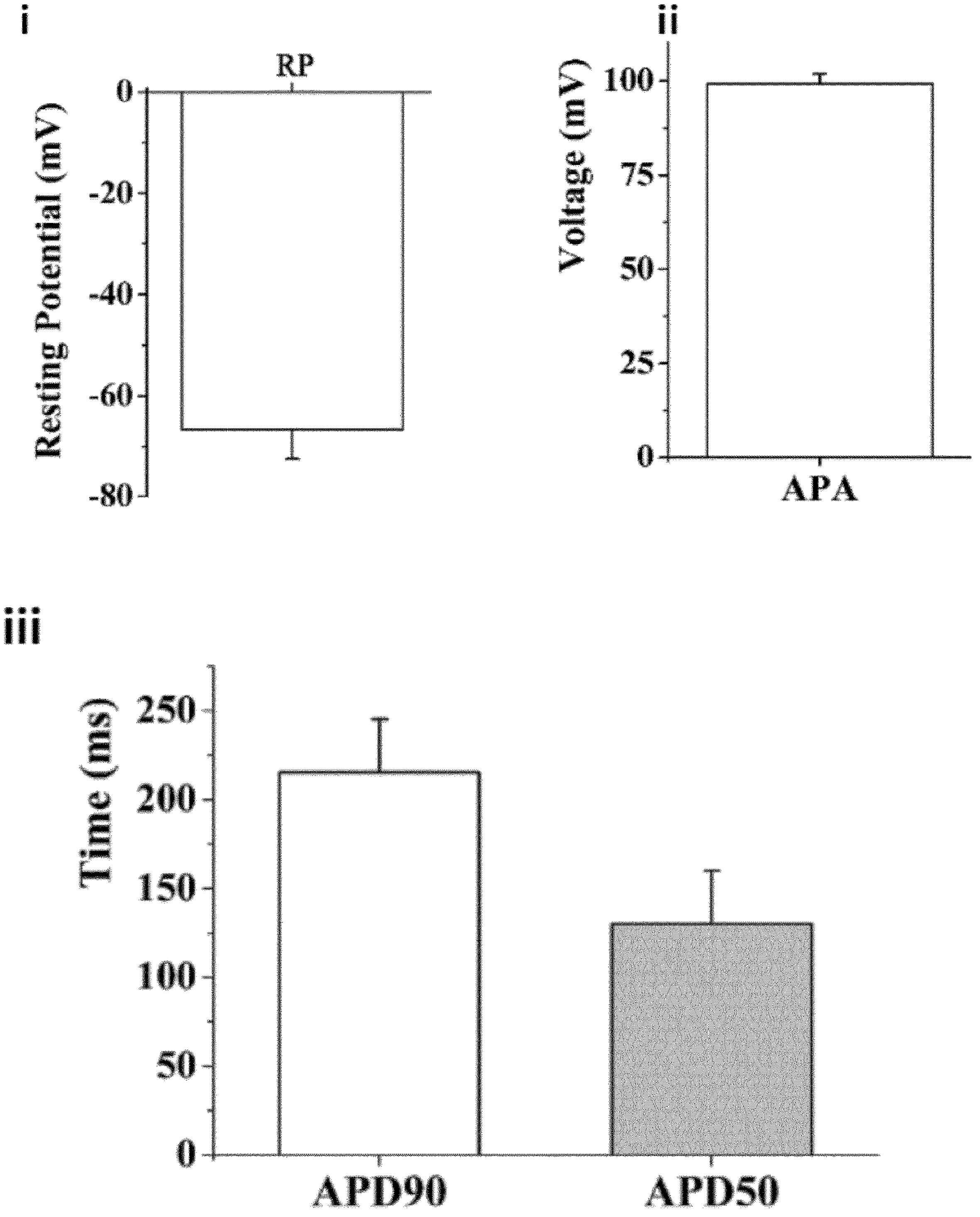
Figure 3C:
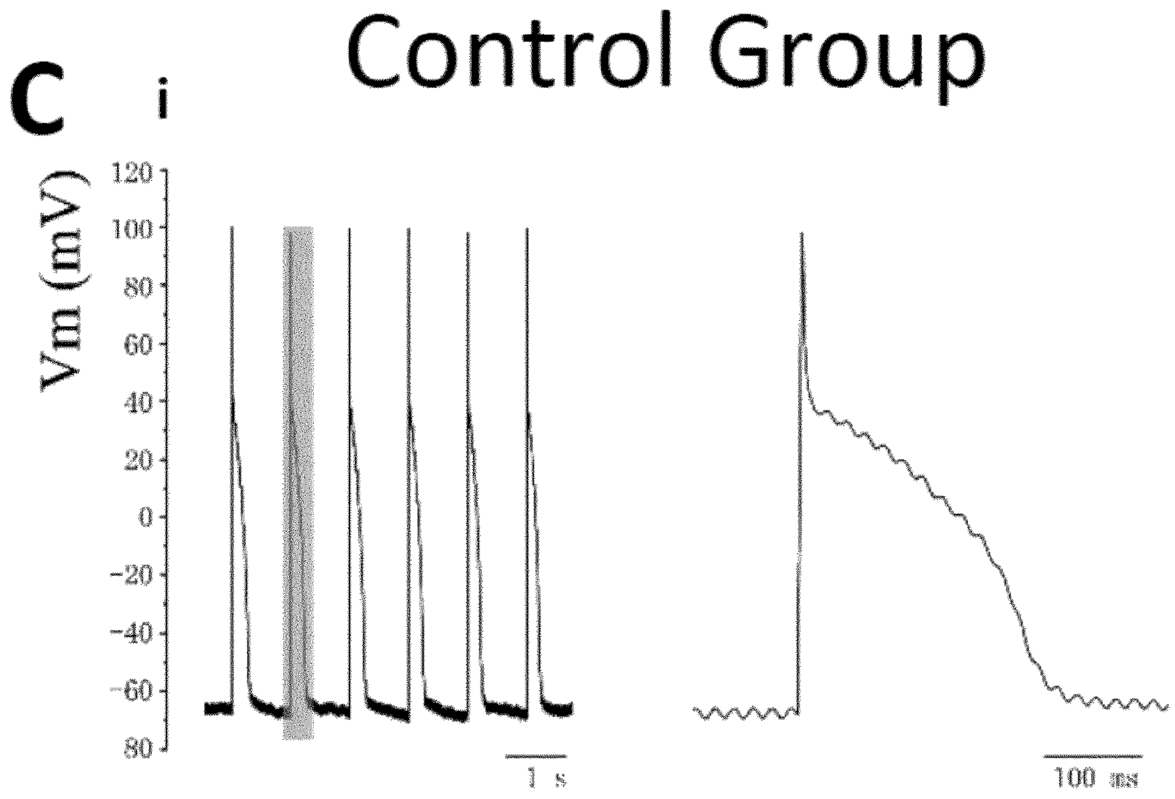
Figure 3D:
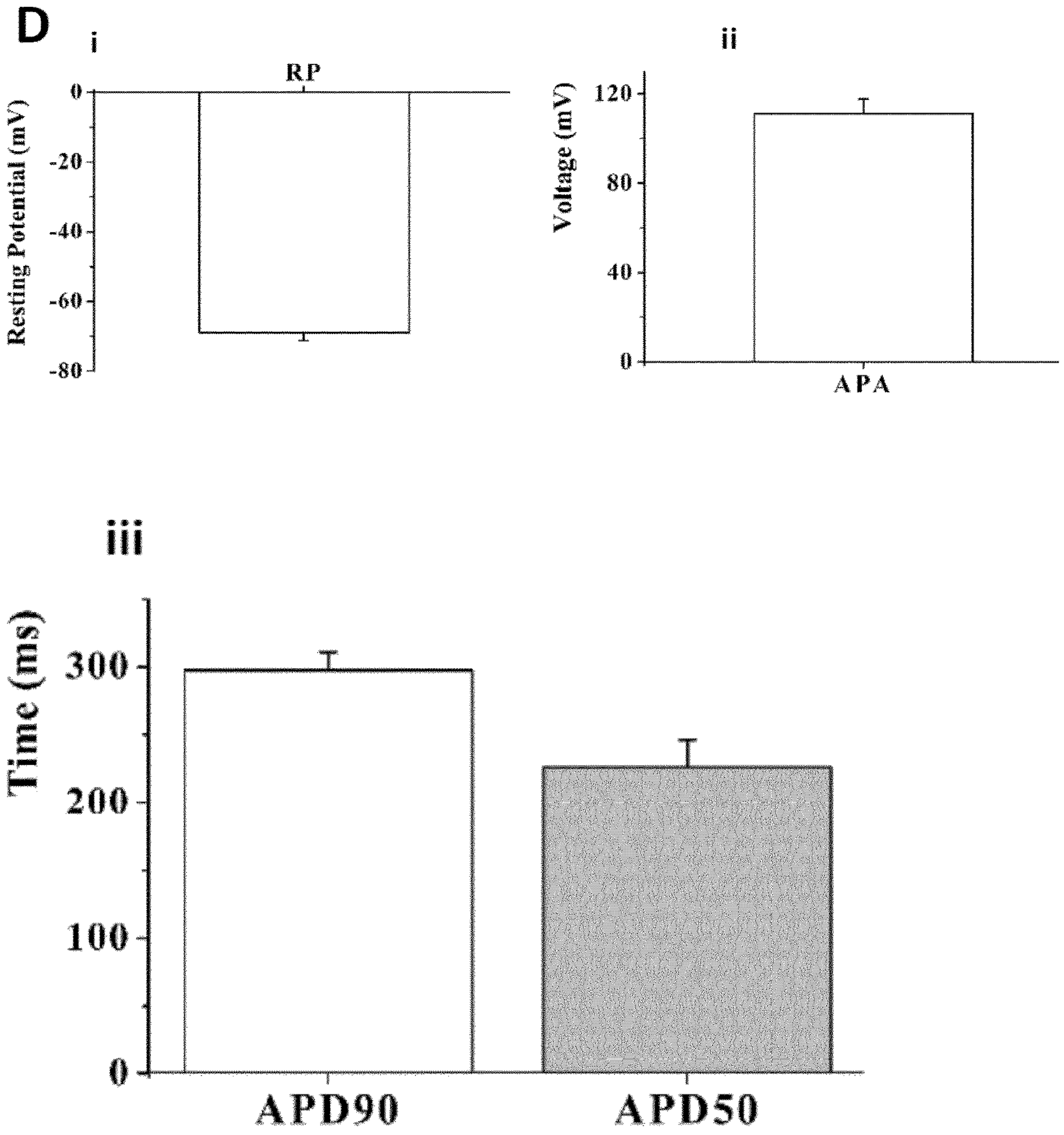

Electrophysiological characteristics were investigated in hiPSC derived atrial cardiomyocytes exposed to the Gremlin2/RA protocol treatment on Day 20-21 of differentiation, and compared with the observations on adult human atrial and ventricular myocytes described above. The cultures were dispersed into individual myocytes as described for the immunohistochemistry experiments reported here (see Examples 1 and 2). Action potential recordings of the experimental group cells were obtained by patch clamp under the whole-cell configuration. Patch clamp results revealed an atrial-type action potential in the experimental group cells as shown in FIG. 3A. Particular atrial characteristics were the absence of a prolonged plateau and relatively rapid repolarization. The action potential duration (APD50) observed in seven experimental group cells was 130±30 ms (n=7). The average resting membrane potential of examined hiPSC derived atrial cardiomyocytes was −67±6 mV (n=7), which is close to that obtained from human atrial CMs −74 mV as previous reported (Grandi et al., 2011). In addition, action potential amplitude (APA) was 99±3 mV (n=7) recorded in iPSC-AMs. This is comparable to that of human adult atrial CMs which is 89±11 mV (n=7).

In summary, the characteristics of action potentials recorded from hiPSC derived atrial cardiomyocytes were broadly similar to those reported for adult human atrial CMs.

Figure 4A:
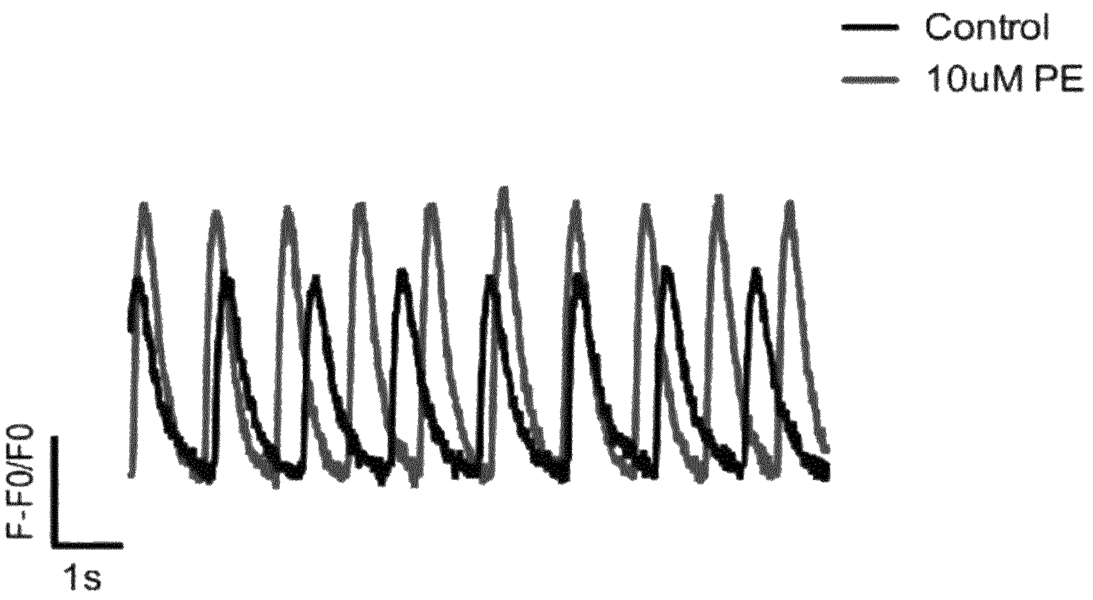
Figure 4A:
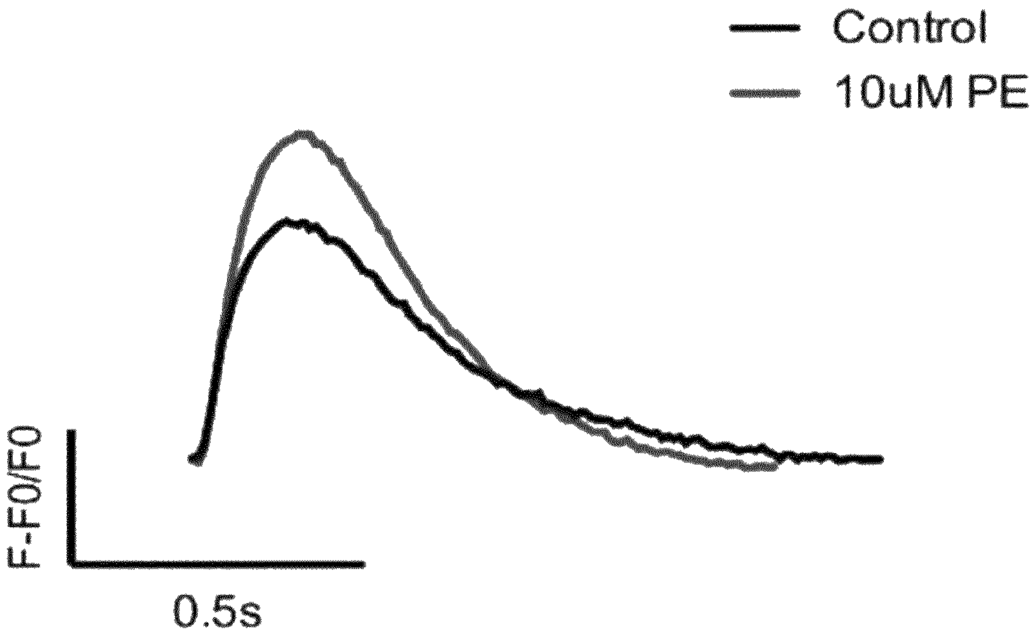

Example 6: α1- and β-Adrenergic Stimulation Increased the Calcium Transient Amplitude in Human iPSC-Derived CMs Receiving Gremlin2/RA Treatment We also tested whether hiPSC derived atrial cardiomyocytes responded to adrenoceptor stimulation by a or p adrenoceptor agonists. The presence of a functional al-adrenoceptor signaling pathway was first tested by exposure of hiPSC derived atrial cardiomyocytes to phenylephrine, which in adult atrial CMs increases the amplitude of $Ca^{2+}$ transients. Phenylephrine is an al-adrenoceptor agonist coupled to $G_q$ and the mechanism of increase in $Ca^{2+}$ transient amplitude is associated with an increase cellular $IP_3$ levels. Atrial cardiomyocytes from Days 25-30 post initiation of differentiating human iPSC derived atrial cardiomyocytes were used to assess the effect of phenylephrine on $Ca^{2+}$ transient amplitude. FIG. 4A/4B shows that 10 μM phenylephrine increased $Ca^{2+}$ transient amplitude by 28±10% as measured from the fluo-4 fluorescence (P<0.05, n=5 batch of cells) but had no effect on the $Ca^{2+}$ transient rise time or decay time. The involvement of α-adrenoceptors was further evaluated by the use 1 μM prazosin, a selective α1 adrenoceptor antagonist, which by itself had no effect on the amplitude of $Ca^{2+}$ transients (P<0.05, n=5 batch of cells).

Figure 4C:
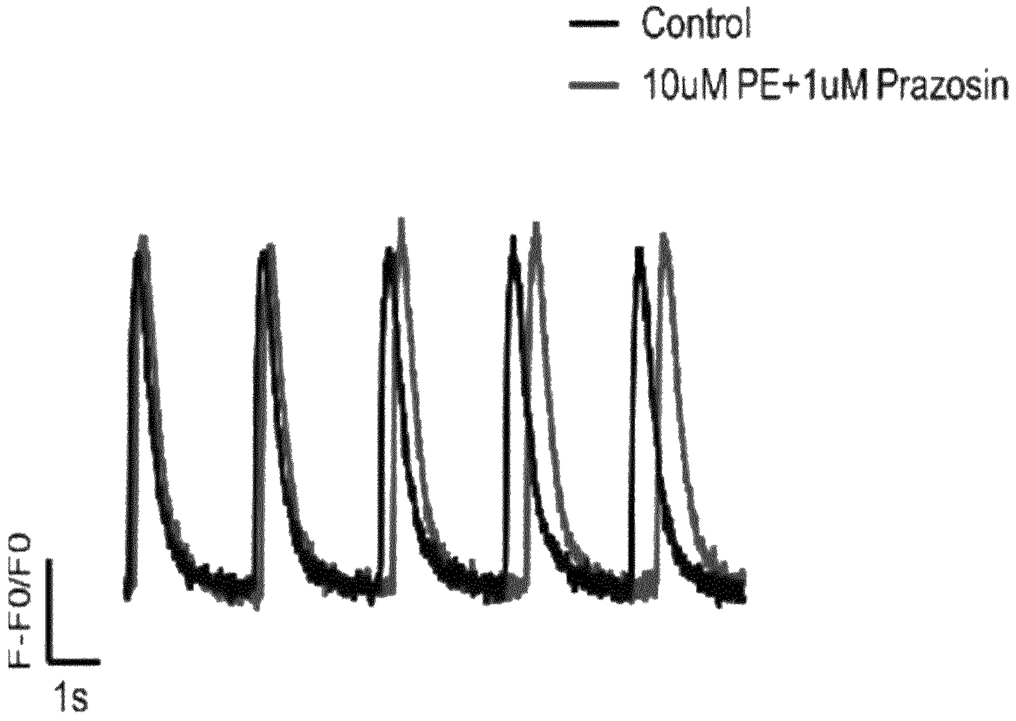
Figure 4C:
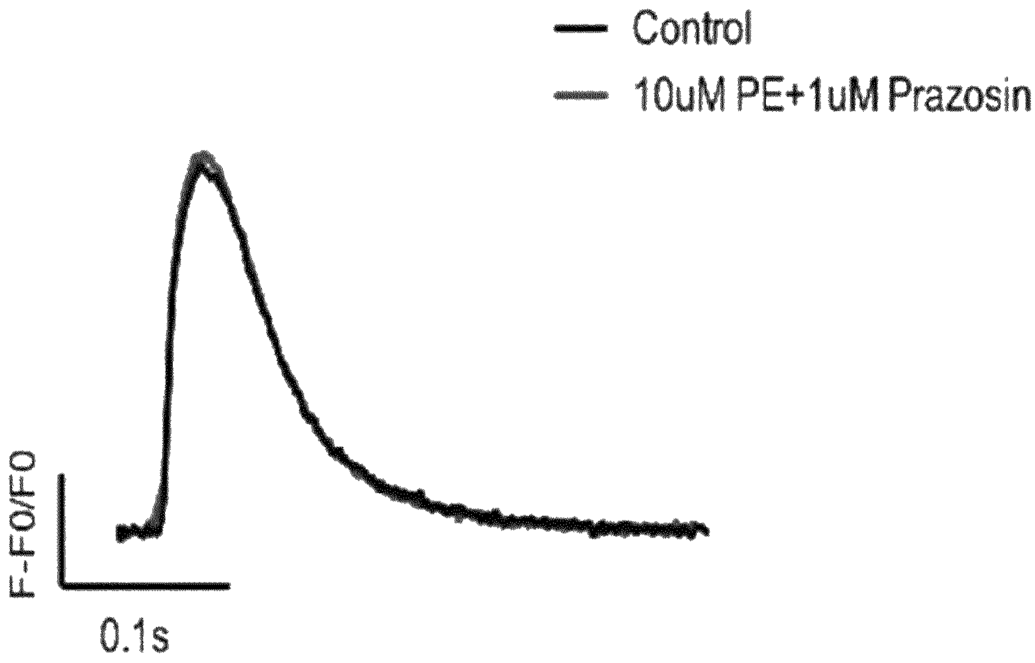
Figure 4D:
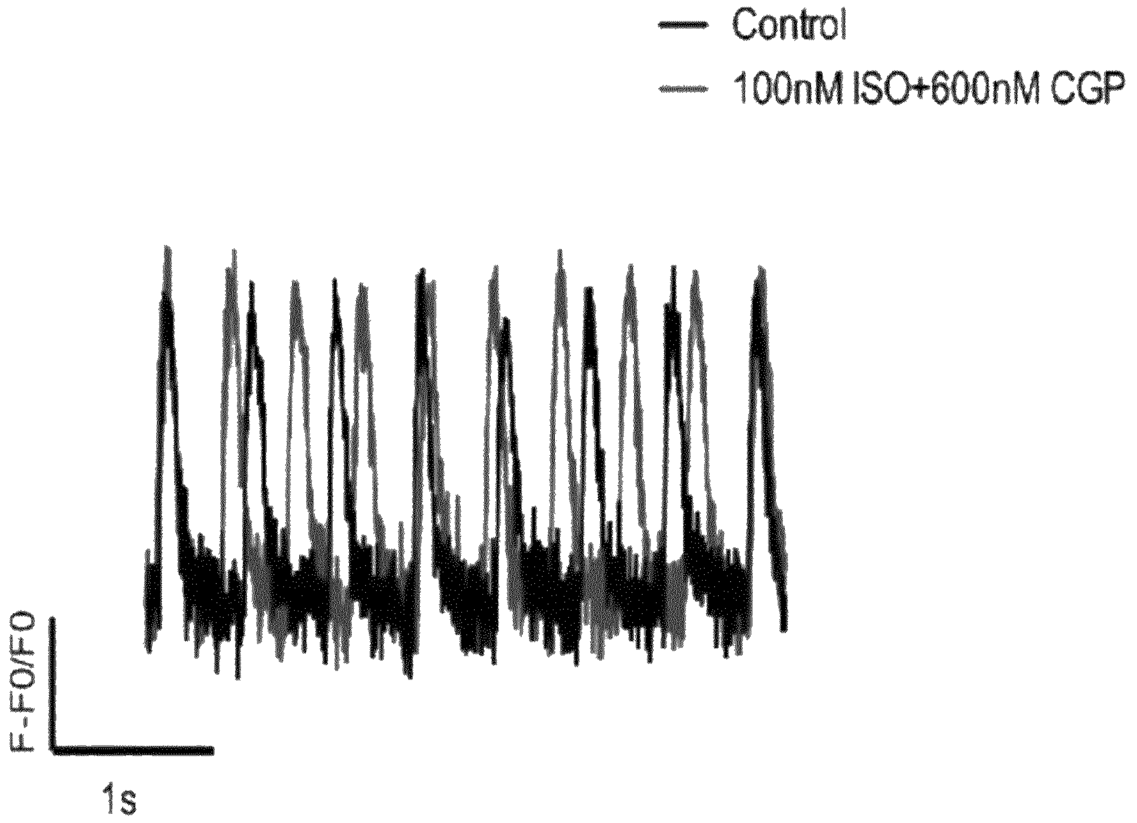
Figure 4D:
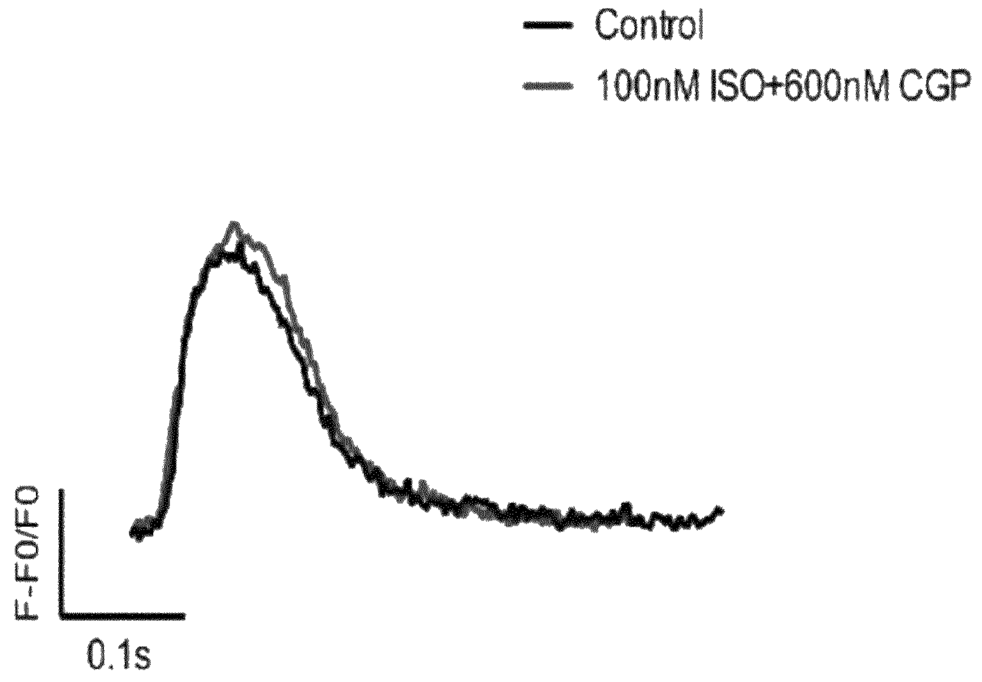

FIG. 4C/4D shows that in the presence of 1 batch of cells prazosin, 10 μM phenylephrine did not cause any significant change in the amplitude of $Ca^{2+}$ transients (P>0.05, n=5 batch of cells), as consistent with blockade of alpha adrenoceptors by prazosin and the consequent suppression of the action of the agonist phenylephrine under these conditions (P<0.05, n=5 batch of cells).

α- and β-adrenergic receptors are highly expressed in human heart, with β-receptors more abundant than α-receptors. β-receptors activate PKA which subsequently phosphorylates L-type $Ca^{2+}$ channels and phospholamban, leading to increased $Ca^{2+}$ influx and $Ca^{2+}$ uptake into the SR (Brodde et al., 1999).

Exposure of hiPSC derived atrial cardiomyocytes to the β-agonist, isoproterenol (100 nM) caused an increase in the amplitude of $Ca^{2+}$ transients of 26±5% % (P<0.05, n=5 batch of cells). The involvement of β1-adrenoceptors in this response was tested by exposure of the cells to a selective β1 antagonist, CGP20712A (300 nM). By itself this antagonist had no effect on the amplitude of $Ca^{2+}$ transients, but when CGP20712A was present, isoproterenol was without effect on the amplitude of $Ca^{2+}$ transients (P>0.05, n=5 batch of cells). It therefore appears that both a and β adrenoceptors are present and functional in hiPSC derived atrial myocytes.

A further experiment was carried out to assess the feasibility of using monolayer HiPSC-AM sheets and optical mapping to assess the feasibility of induction of adrenergic stress induced CaT alternans and arrhythmic events. As shown in FIG. 5, CaT alternans occurred when the preparation was treated by 100 nM ISO at regular pacing at rate of 0.5-1 Hz. The mean signal was segmented into individual beats for calculation of beat to beat CaT50. CaT50 was defined as time between maximum calcium influx velocity and 50% efflux, as reported by the fluorescent indicator.

REFERENCES

Argenziano M, Lambers E, Hong L, Sridhar A, Zhang M, Chalazan B, et al. (2018). Electrophysiologic Characterization of Calcium Handling in Human Induced Pluripotent Stem Cell-Derived Atrial Cardiomyocytes. Stem Cell Reports 10: 1867-1878.

Cyganek L, Tiburcy M, Sekeres K, Gerstenberg K, Bohnenberger H, Lenz C, et al. (2018). Deep phenotyping of human induced pluripotent stem cell-derived atrial and ventricular cardiomyocytes. JCI Insight 3: e99941.

de Vos C B, Pisters R, Nieuwlaat R, Prins M H, Tieleman R G, Coelen R-J S, et al. (2010). Progression From Paroxysmal to Persistent Atrial Fibrillation: Clinical Correlates and Prognosis. Journal of the American College of Cardiology 55: 725-731.

Devalla H D, Schwach V, Ford J W, Milnes J T, El-Haou S, Jackson C, et al. (2015). Atrial-like cardiomyocytes from human pluripotent stem cells are a robust preclinical model for assessing atrial-selective pharmacology. EMBO molecular medicine 7: 394-410.

Feng J, Wible B, Li G-R, Wang Z, & Nattel S (1997). Antisense Oligodeoxynucleotides Directed Against Kv1.5 mRNA Specifically Inhibit Ultrarapid Delayed Rectifier K+ Current in Cultured Adult Human Atrial Myocytes. Circulation Research 80: 572-579.

Giles W R, & Imaizumi Y (1988). Comparison of potassium currents in rabbit atrial and ventricular cells. The Journal of physiology 405: 123-145.

Grandi E, Pandit S V, Voigt N, Workman A J, Dobrev D, Jalife J, et al. (2011). Human atrial action potential and Ca2+ model: sinus rhythm and chronic atrial fibrillation. Circulation research 109: 1055-1066.

Itzhaki I, Maizels L, Huber I, Zwi-Dantsis L, Caspi O, Winterstern A, et al. (2011). Modelling the long Q T syndrome with induced pluripotent stem cells. Nature 471: 225-229.

Müller I I, Melville D B, Tanwar V, Rybski W M, Mukherjee A, Shoemaker M B, et al. (2013). Functional modeling in zebrafish demonstrates that the atrial-fibrillation-associated gene GREM2 regulates cardiac laterality, cardiomyocyte differentiation and atrial rhythm. Dis Model Mech 6: 332-341.

Musunuru K, Sheikh F, Gupta R M, Houser S R, Maher K O, Milan D J, et al. (2018). Induced Pluripotent Stem Cells for Cardiovascular Disease Modeling and Precision Medicine: A Scientific Statement From the American Heart Association. Circulation Genomic and precision medicine 11: e000043.

Oikonomopoulos A, Kitani T, & Wu J C (2018a). Pluripotent Stem Cell-Derived Cardiomyocytes as a Platform for Cell Therapy Applications: Progress and Hurdles for Clinical Translation. Molecular Therapy 26: 1624-1634.

Oikonomopoulos A, Kitani T, & Wu J C (2018b). Pluripotent Stem Cell-Derived Cardiomyocytes as a Platform for Cell Therapy Applications: Progress and Hurdles for Clinical Translation. Mol Ther 26: 1624-1634.

Olson S, Wang M G, Carafoli E, Strehler E E, & McBride O W (1991). Localization of two genes encoding plasma membrane Ca2(+)-transporting ATPases to human chromosomes 1q25-32 and 12q21-23. Genomics 9: 629-641.

Rodriguez P, & Kranias E G (2005). Phospholamban: a key determinant of cardiac function and dysfunction. Arch Mal Coeur Vaiss 98: 1239-1243.

Sakuntabhai A, Ruiz-Perez V, Carter S, Jacobsen N, Burge S, Monk S, et al. (1999). Mutations in ATP2A2, encoding a Ca2+ pump, cause Darier disease. Nat Genet 21: 271-277.

Smyrnias I, Mair W, Harzheim D, Walker S A, Roderick H L, & Bootman M D (2010). Comparison of the T-tubule system in adult rat ventricular and atrial myocytes, and its role in excitation-contraction coupling and inotropic stimulation. Cell Calcium 47: 210-223.

Tanwar V, Bylund J B, Hu J, Yan J, Walthall J M, Mukherjee A, et al. (2014). Gremlin 2 promotes differentiation of embryonic stem cells to atrial fate by activation of the JNK signaling pathway. Stem cells (Dayton, Ohio) 32: 1774-1788.

Wann L S, Curtis A B, January C T, Ellenbogen K A, Lowe J E, Estes N A M, III, et al. (2011). 2011 ACCF/AHA/HRS Focused Update on the Management of Patients With Atrial Fibrillation (Updating the 2006 Guideline): A Report of the American College of Cardiology Foundation/American Heart Association Task Force on Practice Guidelines. Circulation 123: 104-123.

Yamamoto-Hino M, Sugiyama T, Hikichi K, Mattei M G, Hasegawa K, Sekine S, et al. (1994). Cloning and characterization of human type 2 and type 3 inositol 1,4,5-trisphosphate receptors. Receptors Channels 2: 9-22.

Yazawa M, Hsueh B, Jia X, Pasca A M, Bernstein J A, Hallmayer J, et al. (2011). Using iPS cells to investigate cardiac phenotypes in patients with Timothy Syndrome. Nature 471: 230-234.

Zhang Y-H, Wu H-J, Che H, Sun H-Y, Cheng L-C, Li X, et al. (2013). Functional transient receptor potential canonical type 1 channels in human atrial myocytes. Pflügers Archiv—European Journal of Physiology 465: 1439-1449.

SEQUENCES

```
Gremlin2-(human) UniProtKB/Swiss-Prot: Q9H772.1
                                                              SEQ ID NO: 1
  1 mfwklslslf lvavlvkvae arknrpagai pspykdgssn nserwqhqik evlassqeal

 61 vvterkylks dwcktqplrq tvseegcrsr tilnrfcygq cnsfyiprhv kkeeesfqsc

121 afckpqrvts vlvelecpgl dppfrlkkiq kvkqcrcmsv nlsdsdkq
```

The invention claimed is:

1. A process for producing a population of cells which comprises mature atrial cardiomyocytes, the process comprising the step:

(a) treating a first population of cells according to a treatment regimen, wherein the first population of cells comprises iPS cells, and wherein the treatment regimen comprises:

(i) culturing the first population of cells in a first cardiac cell differentiation medium which comprises a moiety which is capable of potentiating the WNT signalling pathway between Day 0 and Day 2;

(ii) culturing the first population of cells in a second cardiac cell differentiation medium which comprises a moiety which is capable of attenuating the WNT signalling pathway between Day 2 and Day 4;

(iii) culturing the first population of cells in a third cardiac cell differentiation medium comprising Gremlin2 between Day 4 and Day 6; and then (iv) culturing the first population of cells in a fourth cardiac cell differentiation medium comprising retinoic acid between Day 6 and Day 10;

such that at least a portion of the iPS cells in the first population of cells differentiate into mature atrial cardiomyocytes, thereby producing a second population of cells which comprises mature atrial cardiomyocytes.

2. A process as claimed in claim 1, wherein the iPS cells are derived from peripheral blood mononuclear cells (PBMCs), fibroblasts or umbilical cord blood $CD34^+$ progenitor cells.

3. A process as claimed in claim 1, wherein at the start of the treatment regimen, all or substantially all of the iPS cells are dissociated into single cells.

4. A process as claimed in claim 1, wherein (i) the first cardiac cell differentiation medium comprises a GSK3B inhibitor; and ii) the second cardiac cell differentiation medium comprises a WNT inhibitor.

5. A process as claimed in claim 1, wherein the first population of cells are contacted with Gremlin2 in the third cardiac cell differentiation medium for 1-3 days or for about 2 days.

6. A process as claimed in claim 1, wherein the first population of cells are contacted with retinoic acid in the fourth cardiac cell differentiation medium for 3-5 days or for about 4 days, after they are contacted with Gremlin2.

7. A process as claimed in claim 1, wherein the process additionally comprises the step:

(b) isolating and/or purifying a portion or all of the mature atrial cardiomyocytes from the second population of cells.

8. A population of cells which comprises mature atrial cardiomyocytes, wherein the population of cells is obtained or obtainable by a process as claimed in claim 1.

9. A purified population of mature atrial cardiomyocytes which is obtained or obtainable by a process of claim 7.

10. The purified population of mature atrial cardiomyocytes as claimed in claim 9, wherein the mature atrial cardiomyocytes have one or both of the following features:

(i) an average resting membrane potential of approximately-67 mV (using a patch clamp method under a whole cell configuration);

(ii) an action potential amplitude of approximately 99 mV.

11. A cell-line derived from the purified population of mature atrial cardiomyocytes of claim 10.

* * * * *